US011666365B2

(12) United States Patent
Rogers

(10) Patent No.: US 11,666,365 B2
(45) Date of Patent: Jun. 6, 2023

(54) STAPLE AND PLATE HARD TISSUE FIXATION

(71) Applicant: Subluxation Safe Asset, LP

(72) Inventor: Diana Rogers, Southwest Ranches, FL (US)

(73) Assignee: Subluxation Safe Asset, LP, Southwest Ranches, FL (US)

( * ) Notice: Subject to any disclaimer, the term of this patent is extended or adjusted under 35 U.S.C. 154(b) by 229 days.

(21) Appl. No.: 16/882,595

(22) Filed: May 25, 2020

(65) Prior Publication Data

US 2020/0281633 A1 Sep. 10, 2020

Related U.S. Application Data

(63) Continuation of application No. 16/016,328, filed on Jun. 22, 2018, now abandoned.
(Continued)

(51) Int. Cl.
*A61B 17/80* (2006.01)
*A61B 17/064* (2006.01)
(Continued)

(52) U.S. Cl.
CPC ........ *A61B 17/809* (2013.01); *A61B 17/0642* (2013.01); *A61B 17/86* (2013.01);
(Continued)

(58) Field of Classification Search
CPC ... A61B 17/809; A61B 17/84; A61B 17/0643; A61B 17/0642; A61B 17/0644;
(Continued)

(56) References Cited

U.S. PATENT DOCUMENTS

| 3,552,389 A | 1/1971 | Allgower et al. |
| 4,278,091 A | 7/1981 | Borzone |

(Continued)

FOREIGN PATENT DOCUMENTS

| DE | 19821680 C1 | 8/1999 |
| DE | 102004015223 A1 | 10/2005 |

(Continued)

OTHER PUBLICATIONS

"4Fusion Shape Memory Implant Operative Technique", Copyright Notice Date: 2015, 12 Pages.
(Continued)

*Primary Examiner* — Amy R Sipp
(74) *Attorney, Agent, or Firm* — Gurr Brande & Spendlove, PLLC.; Robert Spendlove

(57) ABSTRACT

A hard tissue fixation staple-plate interlocking device can include a recess in a staple body or a plate. The device can also include a locking part of the other of the staple body or plate. The device can be reconfigurable between an insertion configuration and an interlocked configuration. In the insertion configuration, the locking part can slide into the recess in a translation sliding motion that is parallel to a sliding motion of the legs of the staple, as the legs of the staple slide through the holes in the plate. In the interlocked configuration, the locking part can be at least partially in the recess, and recess surface portions can engage part surface portions and inhibit movement of the staple and plate out of the interlocked configuration. Also, multiple staples and screws can be interlocked with the plate, with staples being at non-parallel angles to each other.

15 Claims, 23 Drawing Sheets

Related U.S. Application Data

(60) Provisional application No. 62/675,075, filed on May 22, 2018.

(51) Int. Cl.
  *A61B 17/86* (2006.01)
  *A61B 17/00* (2006.01)
  *A61B 17/56* (2006.01)

(52) U.S. Cl.
  CPC ............... *A61B 2017/00526* (2013.01); *A61B 2017/00867* (2013.01); *A61B 2017/564* (2013.01)

(58) Field of Classification Search
  CPC . A61B 17/8061; A61B 17/80; A61B 17/8085; A61B 2017/0641; A61B 2017/0645
  See application file for complete search history.

(56) References Cited

U.S. PATENT DOCUMENTS

| | | | |
|---|---|---|---|
| 4,414,967 A | 11/1983 | Shapiro | |
| 4,589,416 A | 5/1986 | Green | |
| 5,352,229 A | 10/1994 | Goble et al. | |
| 5,395,372 A | 3/1995 | Holt et al. | |
| 5,728,127 A | 3/1998 | Asher et al. | |
| 6,261,291 B1 | 7/2001 | Talaber et al. | |
| 6,966,911 B2 | 11/2005 | Groiso | |
| 8,235,995 B2 | 8/2012 | Focht et al. | |
| 8,679,123 B2 | 3/2014 | Kinmon et al. | |
| 9,017,331 B2 | 4/2015 | Fox | |
| 9,237,911 B2 | 1/2016 | Medoff | |
| 9,839,458 B2 | 12/2017 | Bouduban et al. | |
| 9,924,984 B2 | 3/2018 | Hartdegen et al. | |
| 2002/0173793 A1 | 11/2002 | Allen | |
| 2007/0250065 A1 | 10/2007 | Efron et al. | |
| 2010/0023062 A1* | 1/2010 | Faillace | A61B 17/0642 606/329 |
| 2012/0130374 A1* | 5/2012 | Bouduban | A61F 2/0805 606/75 |
| 2012/0150240 A1 | 6/2012 | Medoff | |
| 2013/0026207 A1 | 1/2013 | Fox | |
| 2013/0231667 A1 | 9/2013 | Taylor et al. | |
| 2014/0018809 A1 | 1/2014 | Allen | |
| 2014/0142628 A1 | 5/2014 | Traynelis et al. | |
| 2014/0276830 A1 | 9/2014 | Cheney | |
| 2014/0277516 A1 | 9/2014 | Miller et al. | |
| 2015/0080969 A1 | 3/2015 | Holly et al. | |
| 2015/0230839 A1 | 8/2015 | Riccione | |
| 2016/0346023 A1 | 12/2016 | Bouduban et al. | |
| 2017/0007305 A1 | 1/2017 | Hollis et al. | |
| 2017/0100163 A1 | 4/2017 | Palmer et al. | |
| 2017/0181779 A1 | 6/2017 | Leither et al. | |
| 2017/0196604 A1 | 7/2017 | Hartdegen et al. | |
| 2017/0303978 A1 | 10/2017 | Palmer et al. | |
| 2017/0311948 A1 | 11/2017 | Morgan et al. | |
| 2018/0036003 A1 | 2/2018 | Bouduban et al. | |
| 2018/0206892 A1 | 7/2018 | Hartdegen et al. | |

FOREIGN PATENT DOCUMENTS

| | | |
|---|---|---|
| EP | 0867149 A1 | 9/1998 |
| WO | 2015144010 A1 | 10/2015 |
| WO | 2017207922 A1 | 12/2017 |

OTHER PUBLICATIONS

"Arthrex Plaple Fixation system Surgical Technique", Copyright Notice Date: 2013, 4 Pages.
"DynaFORCE™ Portfolio—CrossRoads Extremity Systems", accessed at <>, Web Archive Capture Date: Nov. 6, 2017, 8 Pages.
"International Search Report", International Patent Application No. PCT/US19/32931, Application Title: Staple and Plate Hard Tissue Fixation, Notification Date: Jul. 30, 2019, 15 Pages.
"Nickel—Titanium Shape Memory Alloys—Manufacture and Fabrication", retrieved from <>, retrieved on May 15, 2018, 4 Pages.
"Shape Memory Alloy—Nitinol Shape Memory", retrieved from <>, retrieved on May 15, 2018, 2 Pages.

* cited by examiner

STAPLE AND PLATE HARD TISSUE FIXATION

RELATED APPLICATIONS

The present application is a continuation of U.S. patent application Ser. No. 16/016,328, filed on Jun. 22, 2018, which is a non-provisional application claiming the benefit of the filing date of U.S. Provisional Application No. 62/675,075, filed May 22, 2018, both of which are incorporated herein by reference. If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

BACKGROUND

In surgical procedures it is often advantageous to fix a plate to hard tissue such as bone. For example, this may be done in fusing bones together or in adding structural stability to bones that have been broken or otherwise damaged. Plates have been fixed to adjacent bones by threading screws through the plates and into the bones.

SUMMARY

It has been found that current techniques for fixing plates to hard tissue can be improved by fixing plates to bones using staples in addition to or instead of screws. Additionally, novel configurations of staples and plates have been identified that can produce advantageous results in fixing plates to hard tissue.

According to one aspect, a hard tissue fixation system includes a plate defining a pair of holes formed therein, a staple including a body joining a pair of legs of the staple, and a staple-plate interlocking device, which can include features of the staple and the plate. The staple-plate interlocking device can include a recess formed in one of the staple body or the plate, with recess surface portions formed thereon, and with the recess widening as it extends deeper into the recess. The interlocking device can also include a locking part of the other of the staple body or the plate, with the locking part having part surface portions formed thereon. The staple-plate interlocking device can be reconfigurable between an insertion configuration and an interlocked configuration. In the insertion configuration, the locking part can be configured to slide into the recess in a translation sliding motion that is parallel to a sliding motion of the legs of the staple, as the legs of the staple slide through the holes in the plate. In the interlocked configuration, the locking part can be at least partially in the recess, and the recess surface portions can engage the part surface portions and inhibit movement of the staple and plate out of the interlocked configuration, with the legs of the staple extending through the holes in the plate and being configured to extend into hard tissue adjacent to the plate.

According to another aspect, a hard tissue fixation system can include a plate defining a first pair of holes formed therein and a second pair of holes formed therein. A line between centers of the first pair of holes can be at a non-parallel angle to a line between centers of the second pair of holes. The first staple can include a body joining a pair of legs that extend through the first pair of holes and are configured to extend into hard tissue. The second staple can include a body joining a pair of legs that extend through the second pair of holes and are configured to extend into hard tissue.

According to yet another aspect, a plate can be positioned adjacent to hard tissue, with the plate defining a pair of holes formed therein. A staple can be inserted, where the staple can have a pair of legs and a body joining the pair of legs. The inserting of the staple can include inserting the pair of legs of the staple in an insertion direction through holes in the plate and into the hard tissue. A staple-plate interlocking device can be in an insertion configuration during the inserting. A locking part of one of the staple body and the plate, and a recess of the other of the staple body and the plate can slide together in a translation motion in a direction parallel to the insertion direction. The staple-plate interlocking device can be transitioned from the insertion configuration to an interlocked configuration. The interlocked configuration can include the legs of the staple extending through the holes in the plate and into the hard tissue adjacent to the plate. The interlocked configuration can also include the locking part of one of the staple body and the plate being at least partially within the recess in the other of the staple body and the plate. Additionally, the interlocked configuration can include surface portions of the recess engaging with surface portions of the locking part, with the engaging of the surface portions inhibiting movement of the staple and plate out of the interlocked configuration.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

The description and drawings may refer to the same or similar features in different drawings with the same reference numbers.

DETAILED DESCRIPTION

Figure 1:
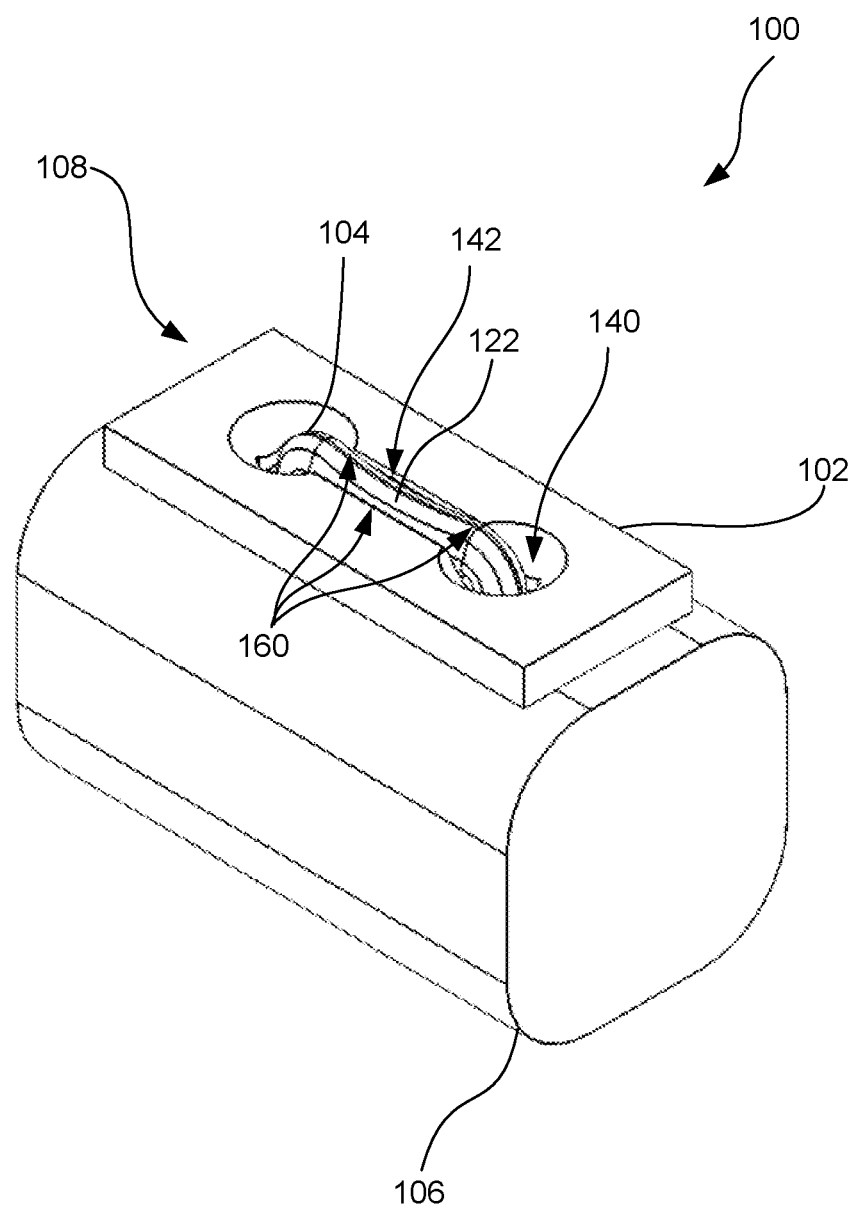
FIG. 1 is a perspective view of a fixation system that is fixed to hard tissue, with the fixation system in an assembled interlocked configuration.

I. Overview of an Example Hard Tissue Fixation System

Referring to FIGS. 1-4, a hard tissue fixation system (100) is illustrated in an interlocked configuration. The fixation system (100) includes a plate (102) and a staple (104), with the staple (104) fixing the plate to hard tissue (106). The hard tissue (106) can be different shapes and sizes, and the plate (102) and staple (104) may also be different shapes and sizes. As is discussed more below, the staple (104) and the plate (102) can be interlocked with each other in multiple different areas of engagement, produced by a staple-plate interlocking device (108), which can include complementary features of the plate (102) and the staple (104). The interlocking device (108) can inhibit movement of the staple (104) and plate (102) out of the interlocked configuration, which can prevent the fixation system (100) from loosening over time and ceasing to properly perform its fixation function. The fixation system (100) can be reconfigured between an insertion configuration, wherein the legs of the staple (104) can slide into corresponding holes in the plate (102), and the interlocked configuration illustrated in FIGS. 1-4. For example, the staple (104) can be inserted into the plate (102) in the insertion configuration, and one or both of the staple (104) and plate (102) can change shape from an unactivated state to an activated state to form the interlocked configuration, so that the staple (104) and plate (102) interlock with each other. Also, as is discussed below with reference to FIGS. 22-23, a plate may include more than two staple-receiving holes, and those holes can be configured to receive staple legs or screws, so that staples and screws can be combined in different configurations to fix the plate to adjacent hard tissue. Such arrangements can produce substantial benefits that are not present in or predictable from prior systems and methods for fixing plates to hard tissue. For example, the staple (104) can compress hard tissue (106) to more securely fix a plate (102) to the hard tissue (106), and the interlocking device (108) can securely hold the staple (104) and plate (102) together, so that the overall fixation system (100) can fix a plate (102) to hard tissue in a secure manner, such as at four or more separate interlocking areas of contact between the staple (104) and plate (102).

The subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently.

II. Features of the Hard Tissue Fixation System

Figure 3:
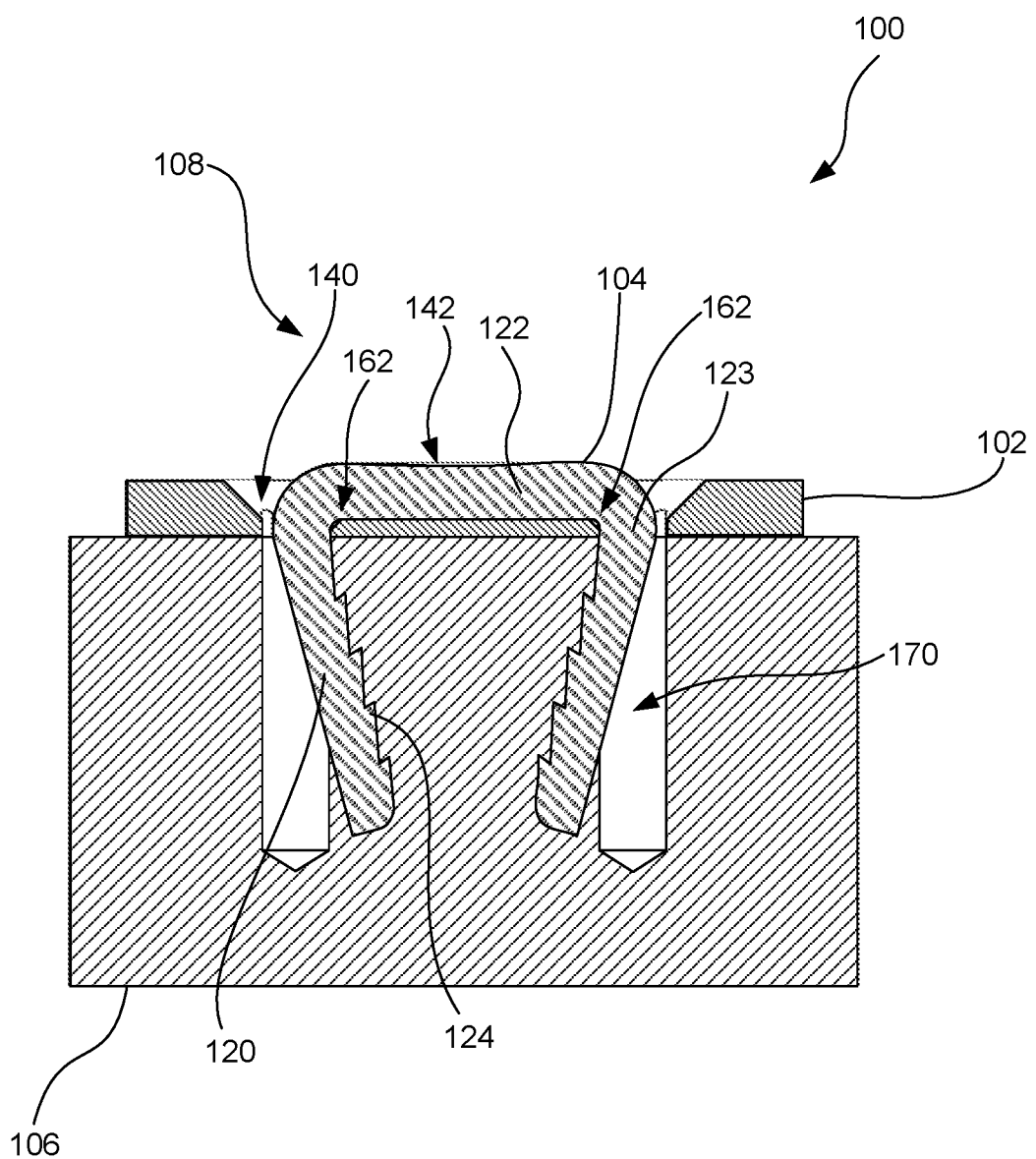
FIG. 3 is a sectional view of the fixation system of FIG. 1 in the assembled interlocked configuration, taken along line 3-3 of FIG. 2.
Figure 4:
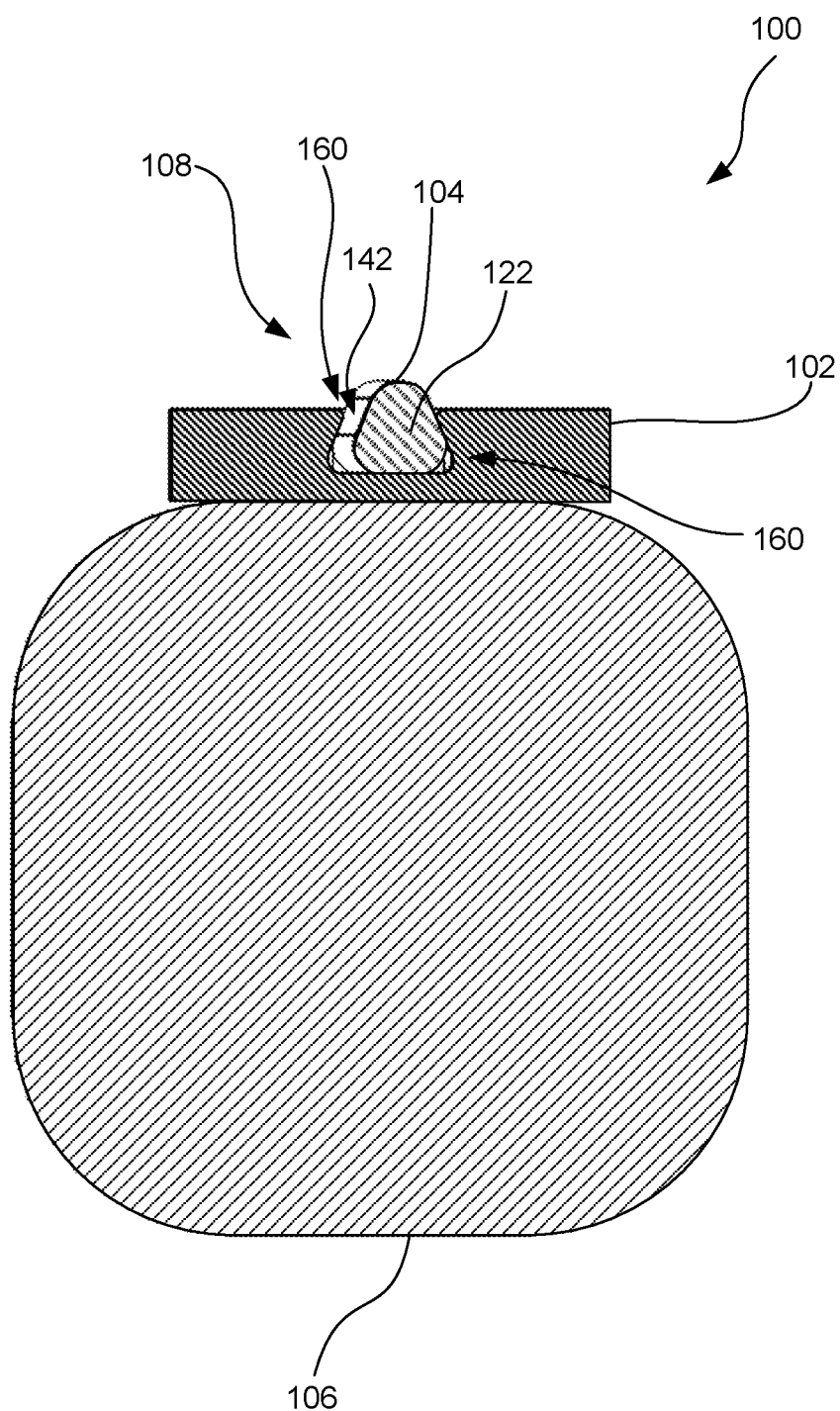
FIG. 4 is a sectional view of the fixation system of FIG. 1 in the assembled interlocked configuration, taken along line 4-4 of FIG. 2.

Referring to FIGS. 5-10, the staple (104) will be described in more detail. The staple (104) can include a pair of legs (120) that are joined by a body (122), which can act as a locking part. Each leg can define barbs (124), which can engage hard tissue (106) to help inhibit movement of the staple (104) out of the hard tissue (106) (see FIG. 3). As can be seen in FIG. 4, the body (122) can widen as it extends in an insertion direction (toward terminal ends of the legs). For example, the body (122) can have a rounded triangular cross section. Each leg (120) can also have a rounded triangular cross section, with a surface on which the barbs (124) are formed facing the opposite leg (120).

Figure 5:
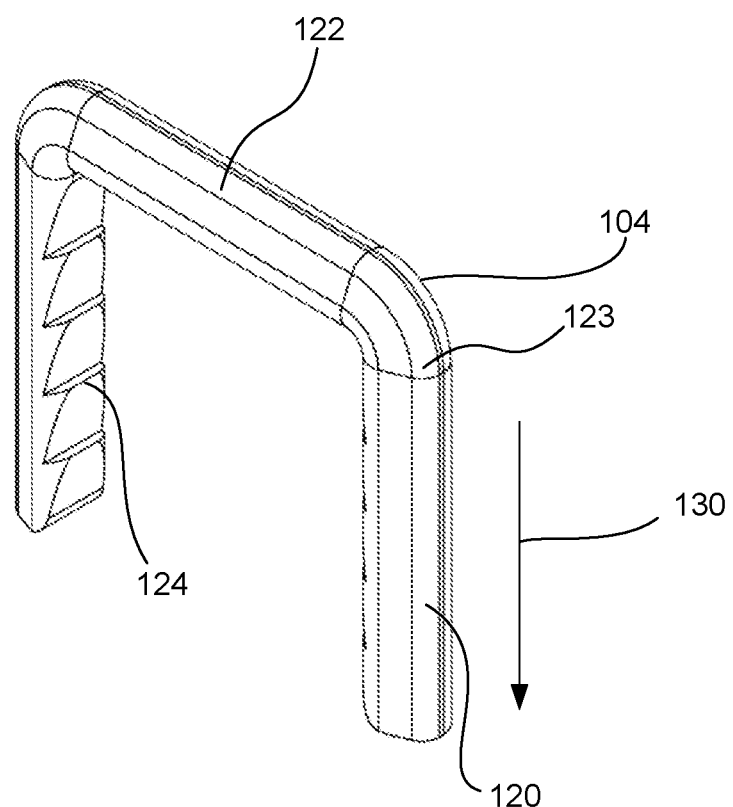
FIG. 5 is a perspective view of a staple of the fixation system of FIG. 1, but with the staple in an unactivated state that can be used for an insertion configuration with a corresponding plate. As used herein, an unactivated state of the staple refers to the staple being in an initial shape that allows it to be inserted, such as into a corresponding plate and/or hard tissue. An activated state of the staple refers to the staple being in a shape that is different from the shape in the initial unactivated state, so that the staple engages hard tissue and/or engages a plate in an interlocked configuration between the staple and plate. The activation of the staple to change the staple from the unactivated state to the activated state may be performed in one or more of different ways, such as releasing tension on the staple and/or changing temperature of a shape memory material staple, as discussed below.
Figure 6:
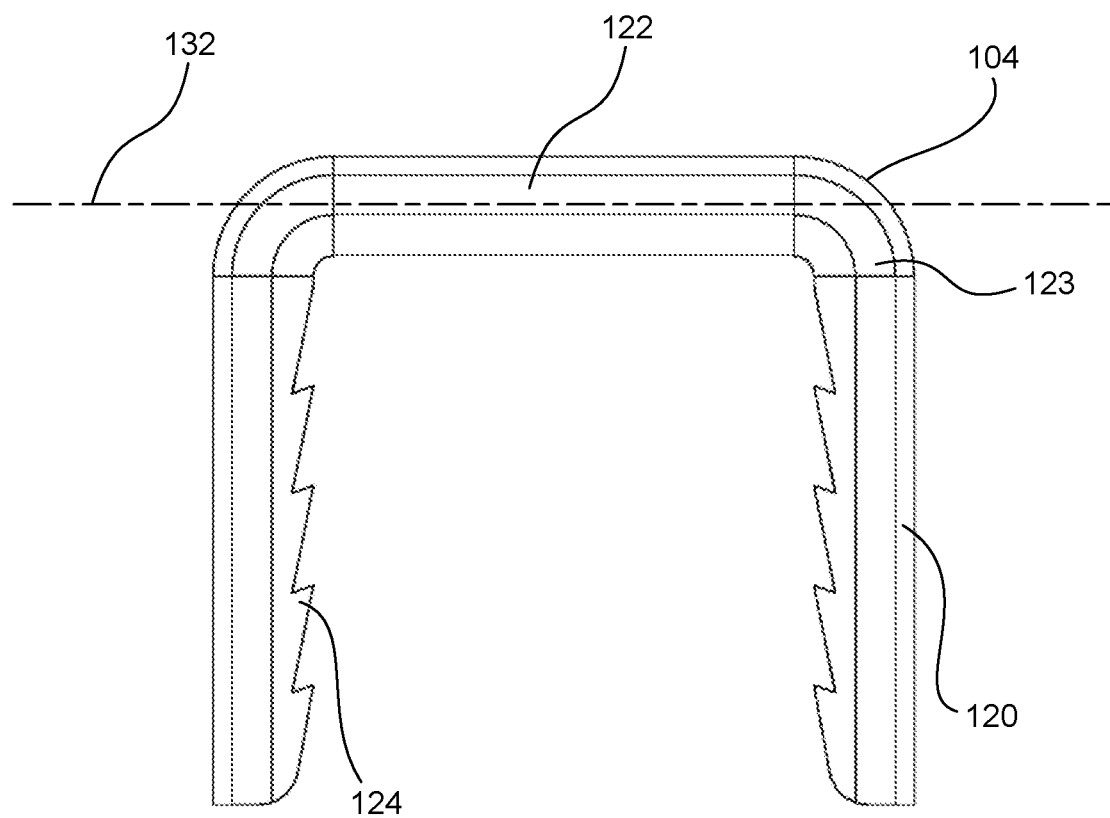
FIG. 6 is a front view of the staple of FIG. 5 in the unactivated state.
Figure 7:
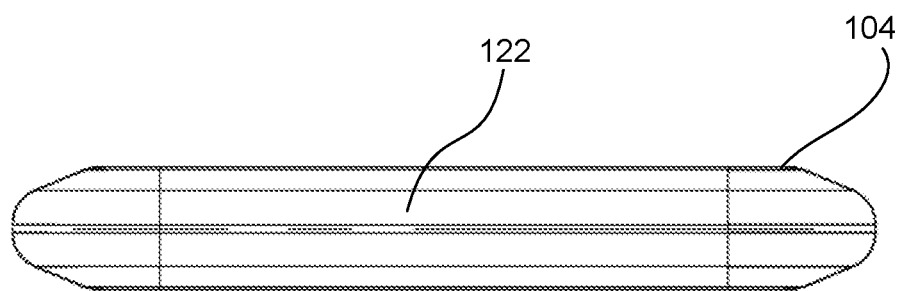
FIG. 7 is a top view of the staple of FIG. 5 in the unactivated state.

FIGS. 5-7 illustrate the staple (104) in the unactivated state, which the staple (104) can be in for the insertion configuration with a corresponding plate (102). In this unactivated state, the staple (104) may be under tension, and is not in the original high temperature shape of the staple (104) to which the staple (104) tends to return in embodiments where the staple (104) is made of shape memory alloy materials. In the unactivated state, the legs (120) can be parallel to each other, extending away from opposite ends of the body (122) in an insertion direction (130) that is perpendicular to the longitudinal axis of the body (122) of the staple (104) (see FIG. 5). The body (122) of the staple (104) can extend between the base portions (123) of the legs (120) without curving, as illustrated, or at least with curvature that is less than in the activated state for the interlocked configuration.

Figure 8:
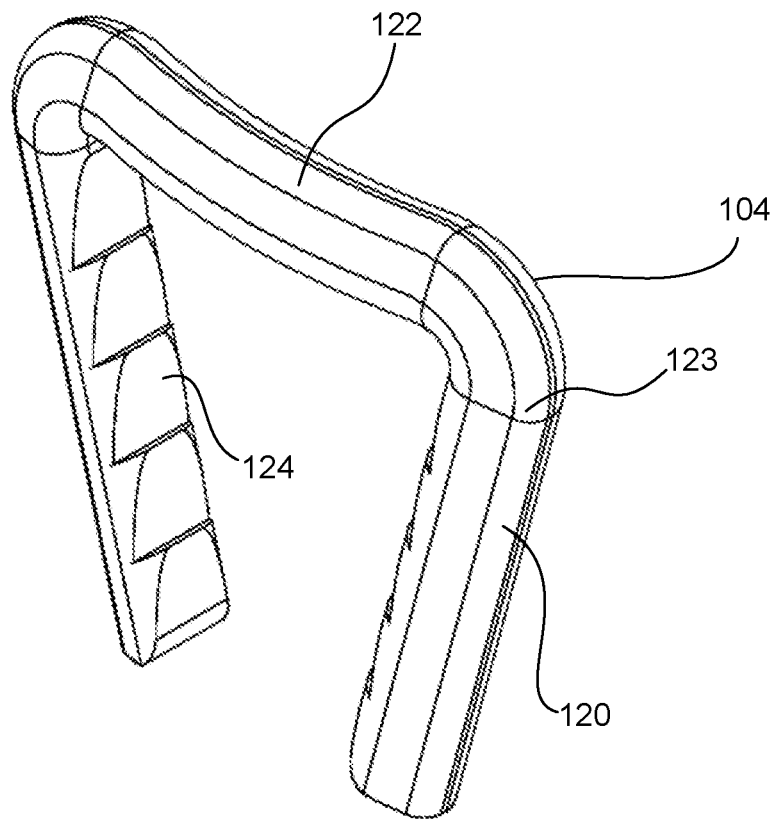
FIG. 8 is a perspective view of the staple of FIG. 5, but with the staple in an activated state that can be used for engaging hard tissue and may also be used for interlocking with a plate in an interlocked configuration after insertion of the staple.
Figure 9:
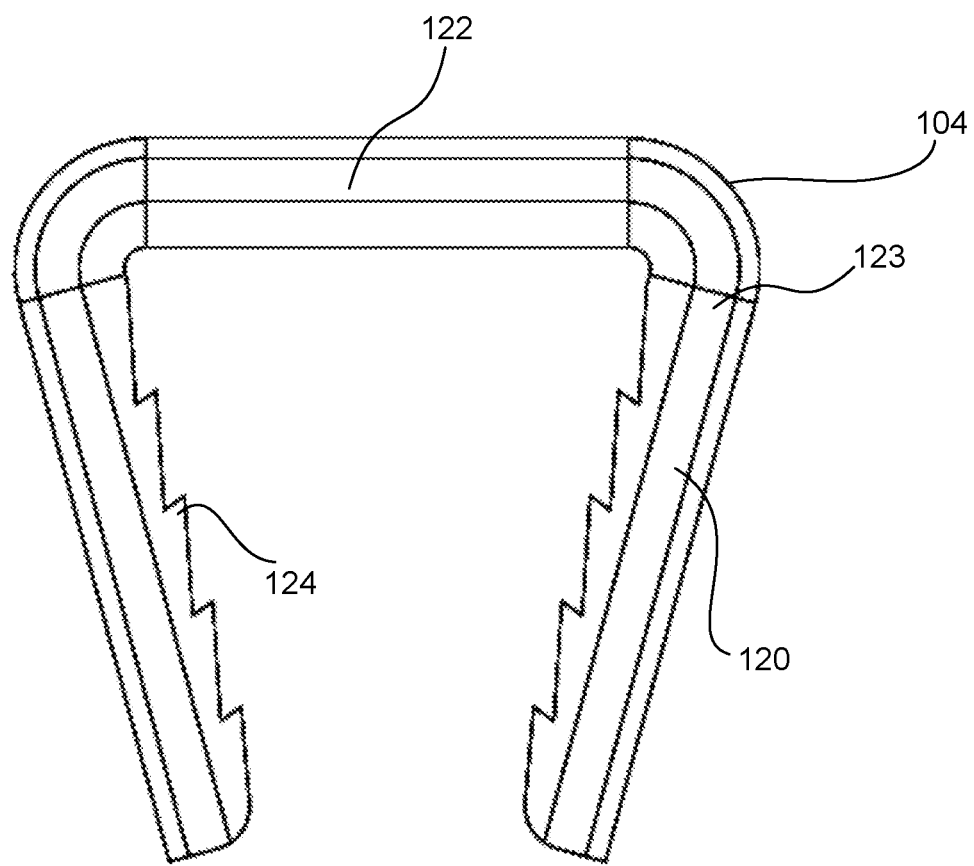
FIG. 9 is a front view of the staple of FIG. 8 in the activated state.
Figure 10:
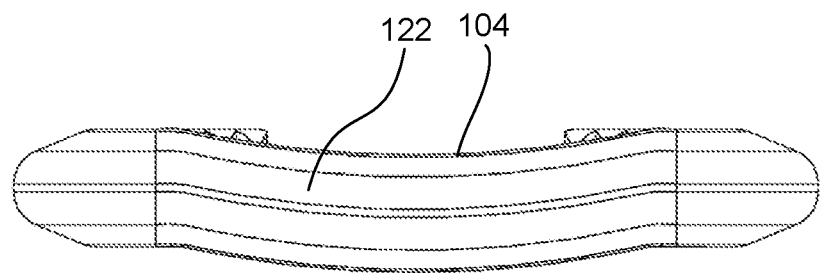
FIG. 10 is a top view of the staple of FIG. 8 in the activated state.

Referring to FIGS. 8-10, the staple (104) is illustrated in an activated state. In this activated state, the legs (120) of the staple (104) can angle inwardly toward each other as they extend generally in the insertion direction (130) away from the body (122) of the staple (104). Additionally, the body (122) of the staple (104) can form a bow, curving in a plane (132) (see FIG. 6) that is generally perpendicular to the insertion direction (130) and parallel to the opposing faces of the plate (102) when the staple (104) is inserted into the plate (102).

As discussed above, the staple (104) can be formed of a shape memory material, for example a shape memory alloy, such as nitinol. The staple (104) may be initially formed using manufacturing techniques such as three-dimensional printing, molding, and/or machining. The staple (104) may then be trained to exhibit the shape in the unactivated state as a temporary shape, and the shape in the activated state as an original shape to which the staple (104) returns. More specifically, objects formed of such shape memory materials can have an "original" shape to which the object will return, such as when the object is heated above a threshold temperature. Using known manufacturing techniques, which can include thermomechanical processing, such objects can be "trained" to return to the original shape when subject to a specific threshold temperature. The threshold temperature may be a range, but it can be adjusted through manufacturing techniques. For example, the threshold temperature for the staple (104) to transform from its unactivated state (FIGS. 5-7), in which it can be delivered to a clinician for use, to its original shape in the activated state (FIGS. 8-10) may be set somewhere between room temperature and the temperature of a living body in which the staple (104) will be implanted during a surgical procedure. For example, the threshold temperature may be a temperature between eighty-five and ninety-five degrees Fahrenheit. The threshold temperature may be reached by allowing the body in which the staple (104) is implanted to heat the staple (104). Also, the threshold temperature of the staple (104) may be reached by actively applying thermal heat to the staple (104) from another source.

Figure 11:
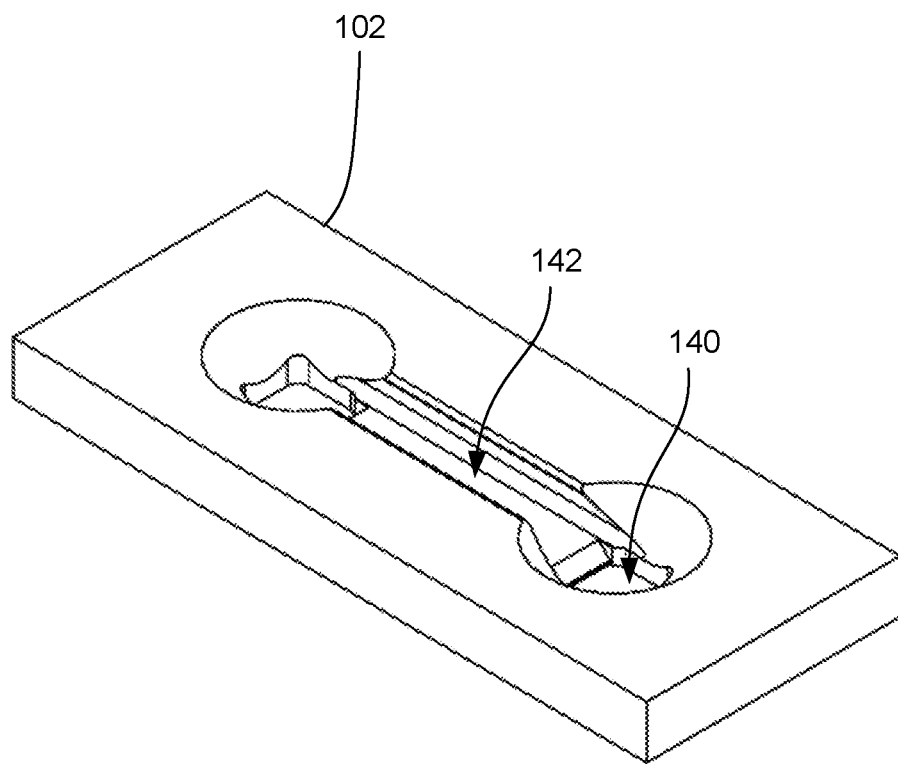
FIG. 11 is a perspective view of a plate of the fixation system of FIG. 1.
Figure 12:
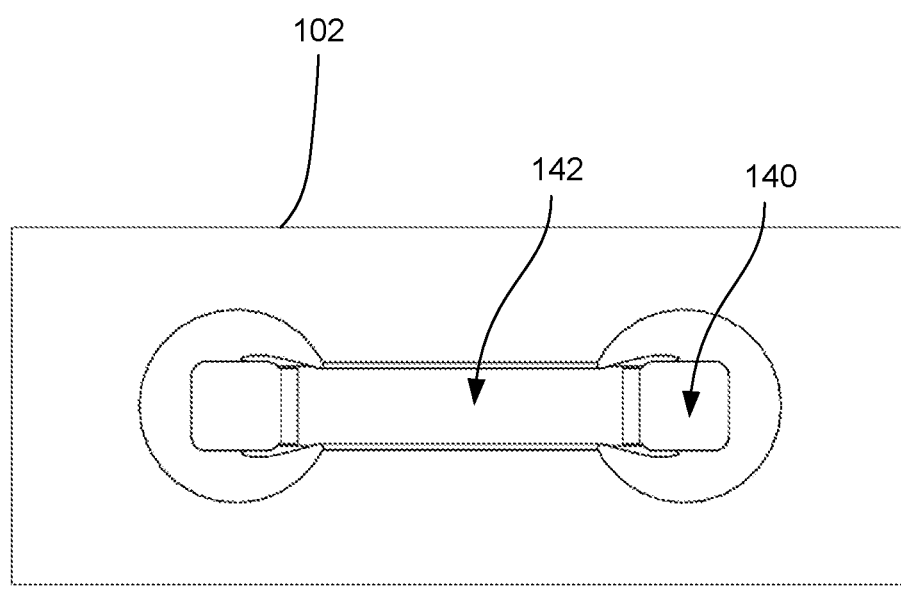
FIG. 12 is a top view of the plate of FIG. 11.

Referring still to FIGS. 1-4 and to FIGS. 11-12, the plate (102) will be discussed in more detail. The illustrated plate (102) is generally rectangular, though many different shapes of plates can be used in accordance with the features discussed herein. Also, the plate (102) is illustrated as being generally flat, or planar, but plates may be utilized that are curved in different shapes appropriate for different applications, such as for being secured to different bones and in different locations.

The plate (102) illustrated in FIGS. 1-4 and FIGS. 11-12 defines a pair of holes (140) passing through the plate (102). The holes (140) can be sized and positioned to receive the legs (120) of the staple (104), with the holes (140) being spaced to match the spacing between the base portions (123) of the legs (120) of the staple (104). Also, the holes (140) can include counterbores or countersinks facing in a top direction (opposite the insertion direction (130)), for receiving matching heads of screws. The holes (140) may also be configured so that threads of screws can engage the material surrounding the holes (140) to "lock" the screws in place relative to the plate (102). Additionally, the plate (102) can define a recess that can be in the form of a groove (142) that extends in the insertion direction (130) into the plate (102) from a second face of the plate (102) (which is opposite the first face of the plate). As the groove (142) extends deeper in the insertion direction (130), the groove (142) can widen. Thus, the groove (142) can have a generally trapezoidal cross-sectional shape (with its opening at the second face of the plate being narrower than its floor, and walls angling from the opening to the floor) that can complement the generally triangular cross-sectional shape of the staple body (122).

The plate (102) can be made of sufficiently rigid and biocompatible materials that are suitable for implanting in living bodies, such as titanium alloys or stainless-steel alloys. The plate can be formed with one or more of various manufacturing techniques, such as three-dimensional printing, molding, and/or machining.

Accordingly, when the fixation system (100) is in the insertion configuration, illustrated in FIGS. 13-17, the legs (120) of the staple (104) can slide through the holes (140) in the plate (102) in the insertion direction (130). With that same translation sliding motion, the body (122) of the staple (104) can slide in the insertion direction (130) into the groove (142) in the plate. As is illustrated, the body (122) of the staple (104) aligns with an opening of the groove (142), and the body (122) has substantially the same curvature as the groove (142) (being straight in the illustrated embodiment).

In contrast, in the interlocked configuration illustrated in FIGS. 1-4, surface portions of the plate (102) and the surface portions of the staple (104) can engage each other at multiple separate engagement areas. Specifically, the engagement areas can include three body engagement areas (160) (see FIGS. 1-2) where surface portions of the body (122) of the staple (104) engage surface portions of the groove (142) in the plate (102), with one body engagement area (160) at each end of the body (122) on one side of the body (122) and another body engagement area (160) in the middle of the body (122) on an opposite side of the body (122). These body engagement areas (160) can be formed by the curvature of the body (122) along the plane (132) in the activated state of the staple (104) for the interlocked configuration, which curvature is different from the straight curvature of the groove (142), resulting in the body (122) being misaligned with the groove (142). The engagement areas can also include pinching engagement areas (162) near the inner base portion (123) of each leg (120), where the leg (120) is bent inwardly at the base portion (123) of the leg (120) in the activated state of the staple (104) for the interlocked configuration to pinch the plate (102) between the legs (120) (see FIG. 3). Accordingly, the staple (104) and plate (102) can interlock to engage each other in five engagement areas (three body engagement areas (160) and two pinching engagement areas (162)).

The interlocking device (108) can include the surface portions of the plate (102) and the surface portions of the staple (104) that form the body engagement areas (160) and the pinching engagement areas (162). The interlocking device (108) can further include the body (122) of the staple, and at least the base portions (123) of the legs (120) of the staple (104). The interlocking device (108) can further include the material of the plate (102) that defines the groove (142), including the material that engages the engaging surface portions of the body (122) of the staple (104) and the material that is pinched between the surface portions of the legs (120) of the staple (104) (with the pinching also involving surface portions of the body (122) of the staple (104)).

The hard tissue fixation system may include different configurations of the staple and the plate, as compared to the specific configurations illustrated in the attached figures for the hard tissue fixation system (100). As one example, the interlocking recess and locking part may be different from the groove in the plate acting as the recess to receive the staple body acting as the locking part in the discussion above, so long as a recess is in one of the staple body or the plate, and the locking part is in the other of the staple body or the plate. For example, the staple and plate may be reconfigured so that the staple defines a recess into which a protruding part of the plate fits. In such a configuration, the staple and/or the plate may change shape between an insertion configuration and an interlocked configuration. For example, the plate may define a rail that fits into a recess (such as a groove) formed in the body of the staple. The curvature of the rail and the recess may match each other in the insertion configuration, so that the rail can fit into the recess as the staple is inserted through holes in the plate. The shape of the plate and/or staple can change in the interlocked configuration (e.g., using shape memory material) so that the rail engages the material forming the recess. Also, a shape-changing part such as the body (122) may have less curvature in the interlocked configuration than in the insertion configuration, such as where the mating part that does not change shape has more curvature (for example, a curved staple body can match the curvature of a curved groove in the plate in the insertion configuration but can reduce its curvature to interlock with the material defining the curved groove in the interlocked configuration).

III. Example of Use of a Hard Tissue Fixation System

Figure 13:
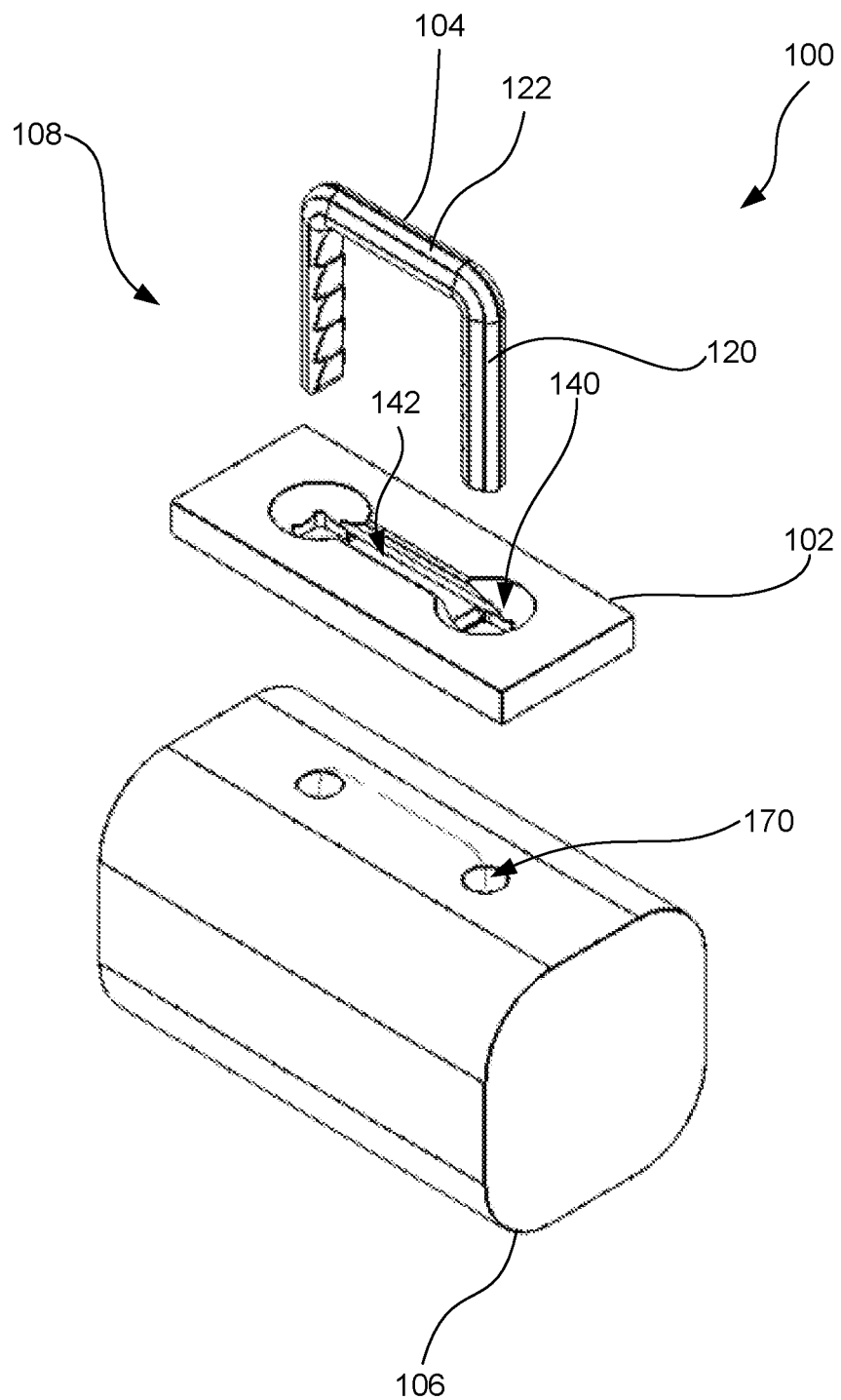
FIG. 13 is an exploded perspective view of the fixation system of FIG. 1, but with the system assembled in an insertion configuration.
Figure 14:
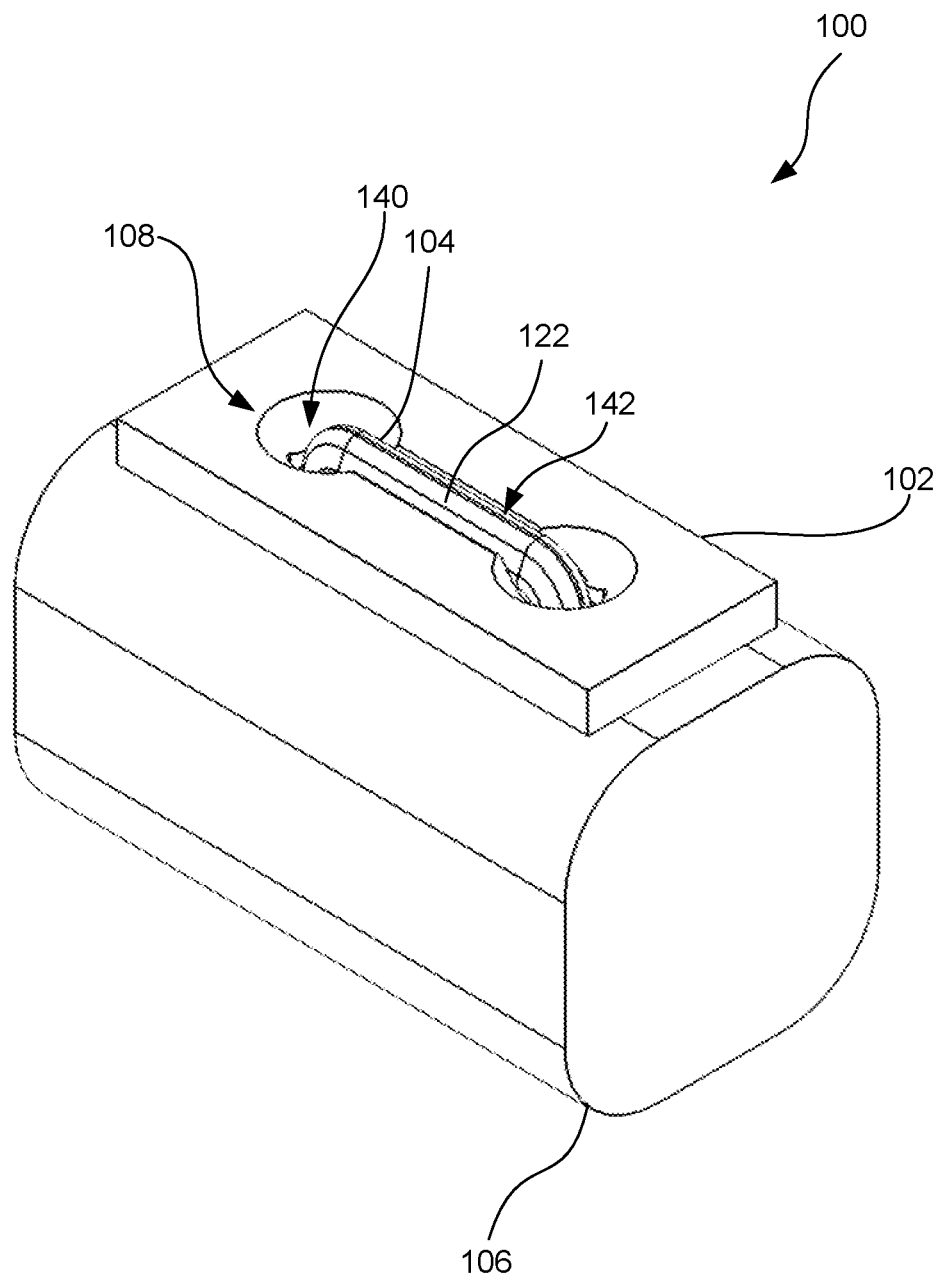
FIG. 14 is an assembled perspective view of the fixation system of FIG. 13, assembled and still in the insertion configuration (i.e., without being interlocked).
Figure 15:
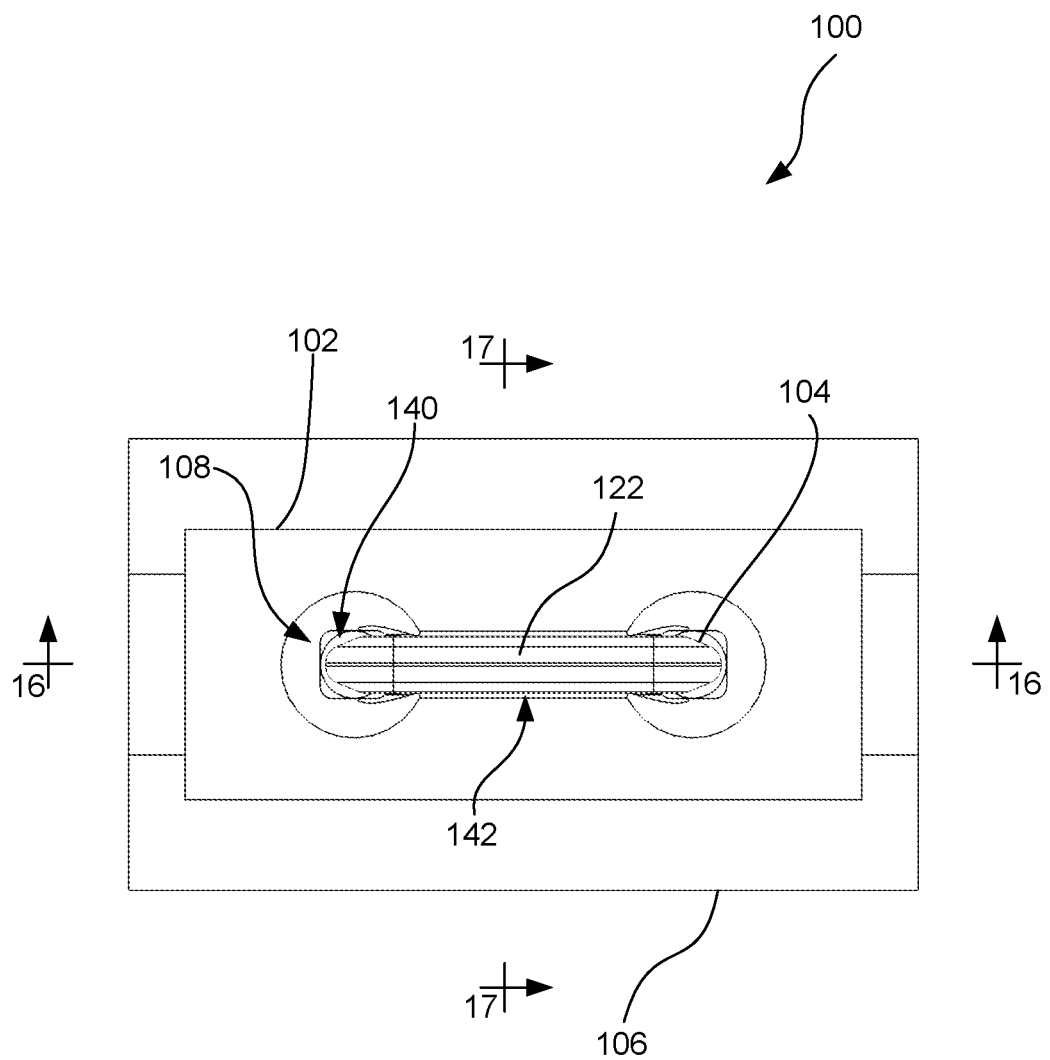
FIG. 15 is a top view of the assembled fixation system of FIG. 14 in the insertion configuration.
Figure 16:
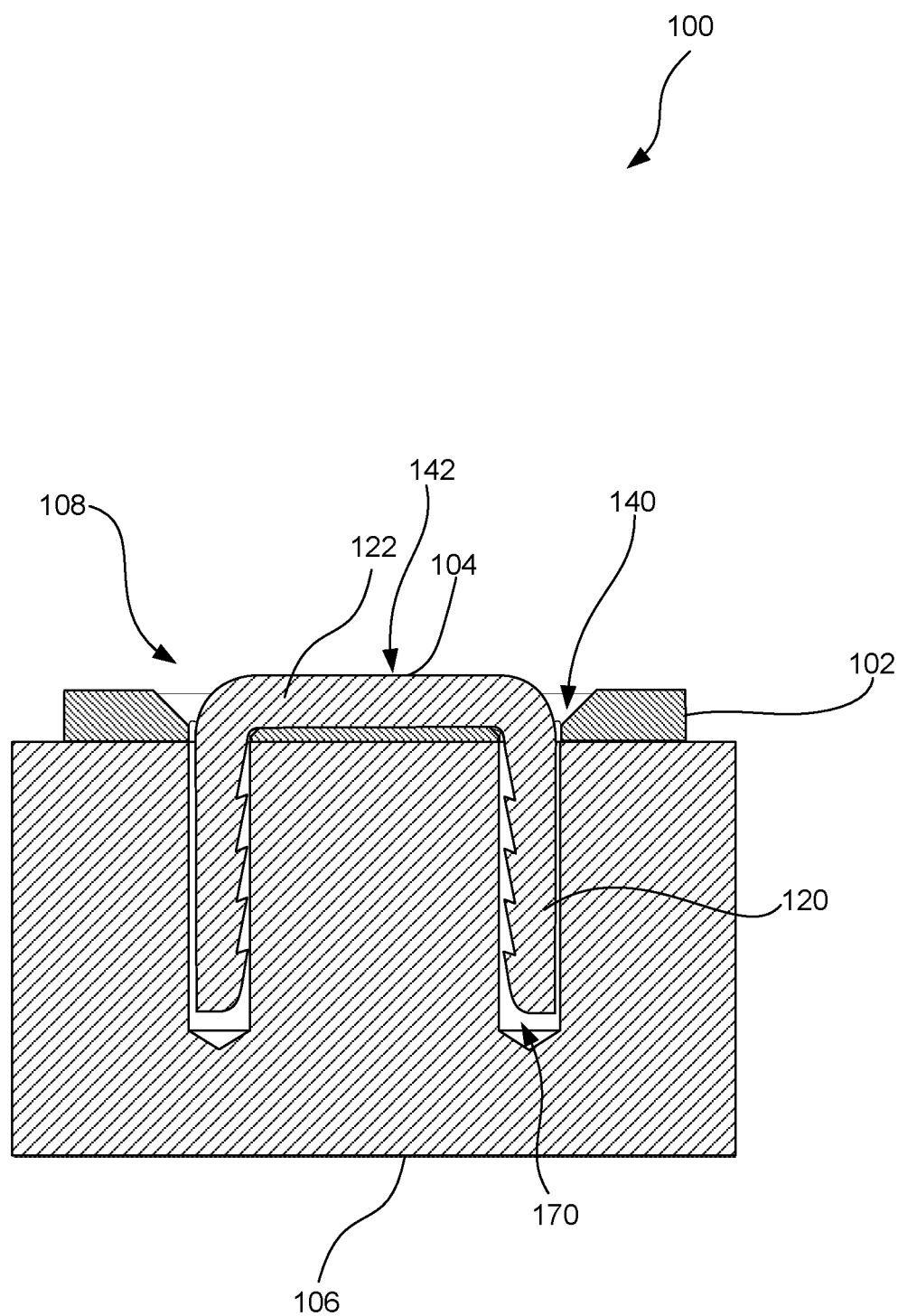
FIG. 16 is a section view of the fixation system of FIG. 14 in the assembled insertion configuration, taken along line 16-16 of FIG. 15.
Figure 17:
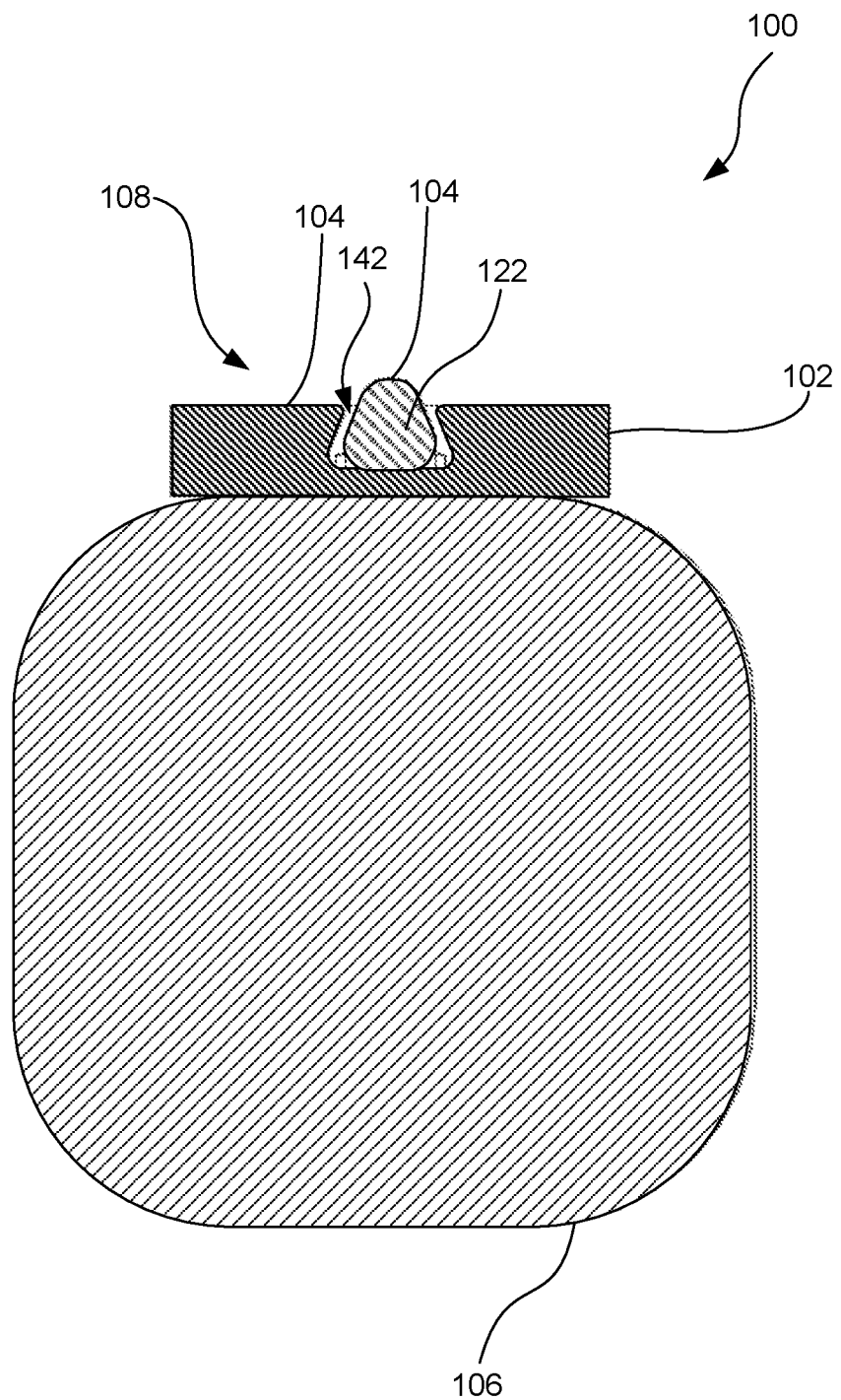
FIG. 17 is a sectional view of the fixation system of FIG. 14 in the assembled insertion configuration, taken along line 17-17 of FIG. 15.

Use of the hard tissue fixation system (100) will now be discussed. Referring to FIG. 13, a surgical procedure can include drilling pilot holes (170) in the hard tissue (106) that are spaced and sized to receive the legs (120) of the staple (104) (for embodiment with screws as discussed below, holes for screws may also be drilled). The plate (102) can be positioned with the holes (140) in the plate aligning with the pilot holes (170), with a first face of the plate being adjacent to the hard tissue (106), such as abutting the hard tissue (106). The staple (104) can be held with a staple insertion device (not shown), such as staple insertion devices that have been used previously to insert staples in hard tissue during surgical procedures. Using the staple insertion device, a clinician can slide the staple (104) in the insertion direction (130) toward the plate (102), to slide the legs (120) of the staple through the holes (140) in the plate and into the pilot holes (170) in the hard tissue (106). This translation sliding motion in the insertion direction (130) can continue until the body (122) of the staple (104) is seated in the groove (142), and the clinician can actuate the staple insertion device to release the staple (104). If the staple (104) is not sufficiently inserted after it is released from the insertion device, a clinician may use a tamp tool (or hammer) to tamp the staple (104) further in the insertion direction (130) relative to the plate (102), so that the staple is in the position illustrated in FIGS. 14-17. The staple (104) can activated, such as by heating the staple (104) to its threshold shape memory temperature. For example, this may be done by applying active heat to the staple (104), applying electrical current to the staple (104) and/or allowing the body into which the staple (104) is implanted to heat the staple (104). This can result in the staple (104) transitioning from its unactivated state to its original interlocked shape in its activated state, resulting in the interlocked configuration illustrated in FIGS. 1-4 and discussed above.

In addition to this transition to the interlocked configuration being operable to interlock the staple (104) and plate (102) together (including the compressing of the plate (102) between the legs (120) of the staple (104)), the movement of the legs (120) of the staple (104) toward each other can compress the hard tissue (106) between the legs (120). For example, this is illustrated in FIG. 3, showing the legs (120) having moved from the pilot holes (170) and into the hard tissue (106) between the pilot holes (170). This compression can help to inhibit movement of the staple (104) out of the hard tissue (106), thereby providing a more solid fixation of the plate (102) to the hard tissue (106).

IV. Examples of Staples with Additional Legs

Figure 18:
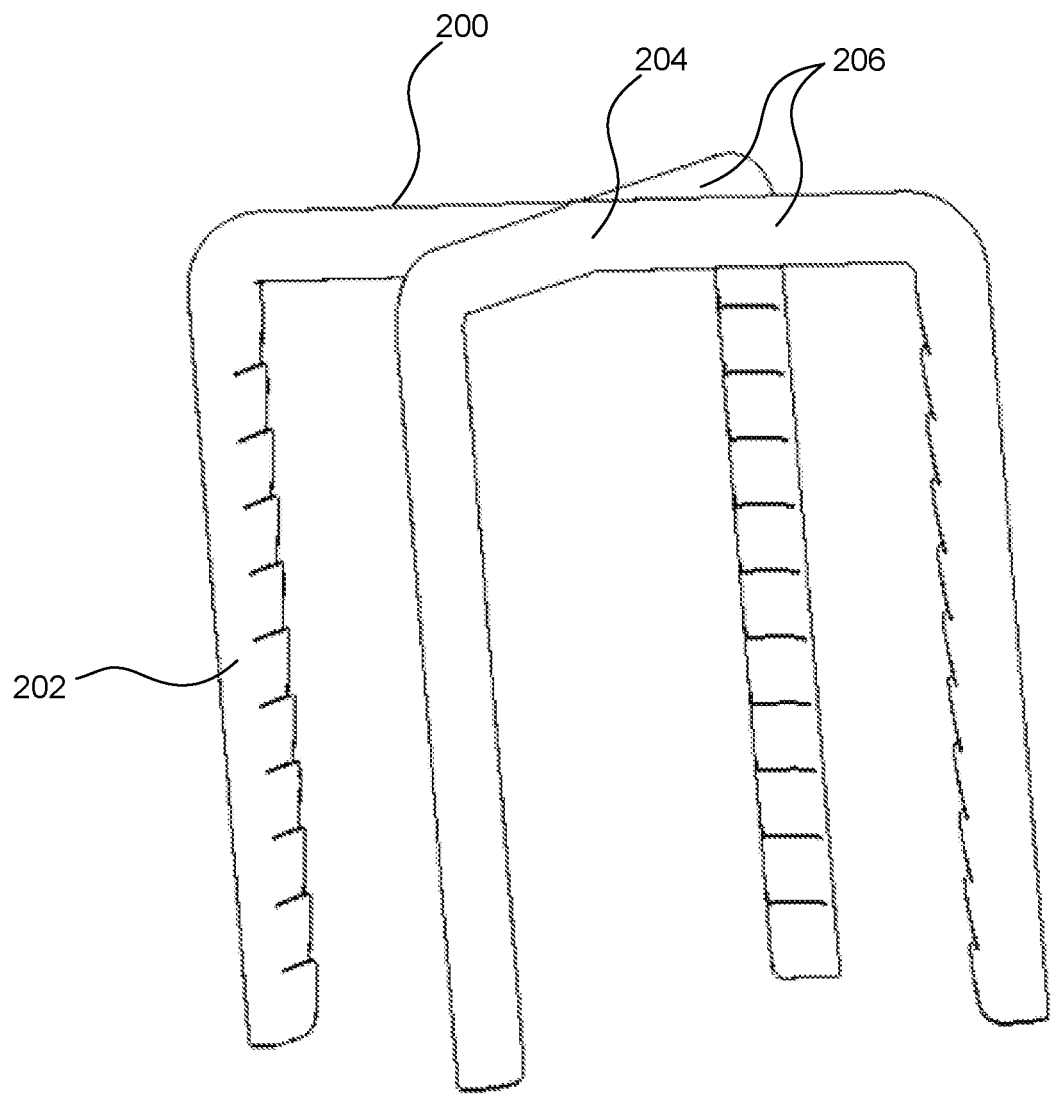
FIG. 18 is a perspective view of a four-prong staple in an unactivated state.
Figure 19:
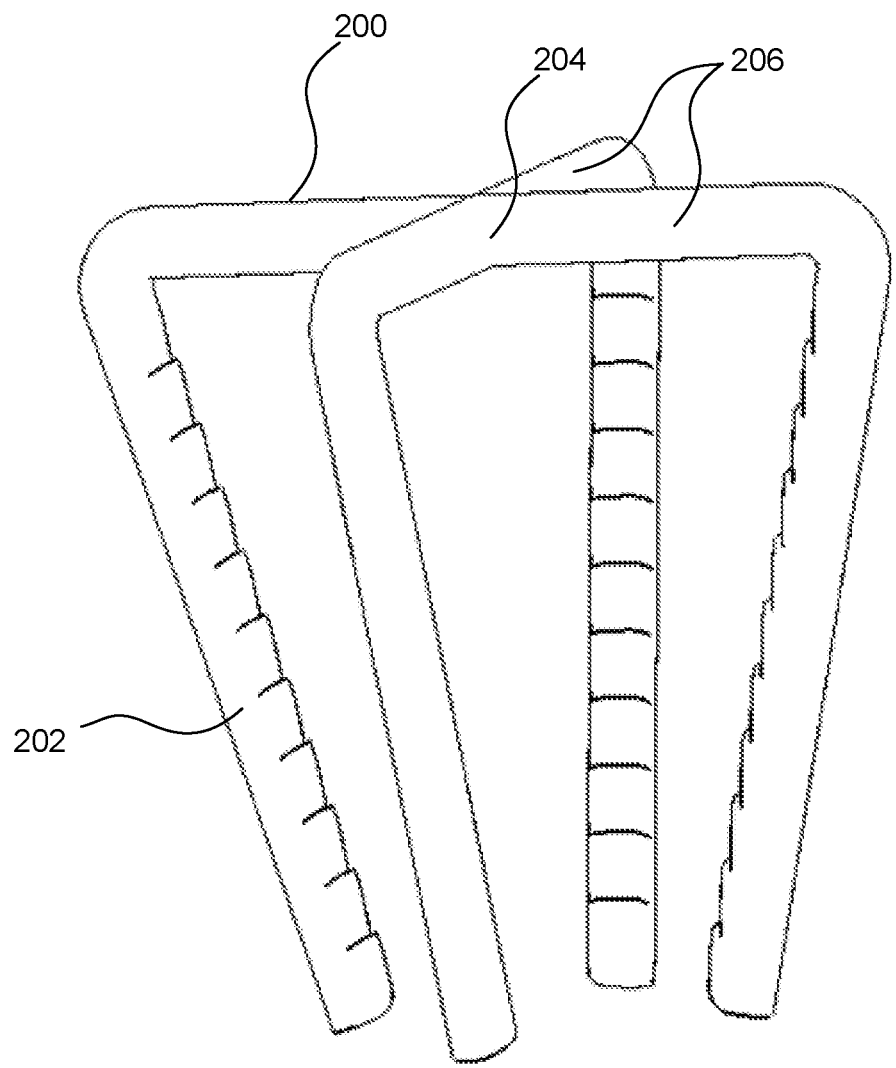
FIG. 19 is a perspective view of the four-prong staple of FIG. 18 in an activated state.

Referring now to FIGS. 18-19, another embodiment of a staple (200) will be discussed. The staple (200) can be a four-pronged staple that has four legs (202). The legs (202) can be joined by a body (204) that can include a pair of crossing beams (206) that each extends between a pair of the legs (202). The beams (206) can be perpendicular to each other, so that the staple (200) includes two two-pronged staple structures that each includes one pair of legs (202) joined by a beam (206). The two beams (206) can be joined at their midpoints to form the overall staple (200). FIG. 18 illustrates an unactivated state, which can be used for an insertion configuration with a plate, for the staple (200), where the legs (202) are perpendicular to each other, with the legs extending in an insertion direction that is substantially perpendicular to a plane that includes both of the beams (206).

The staple (200) can transform to the activated state illustrated in FIG. 19, where the legs (202) angle inwardly toward each other as they extend in the insertion direction from the body (204). For example, with each leg pair that is joined by a beam (206), the legs (202) can angle inwardly toward each other as they extend in the insertion direction from the body (204). The staple (200) may be integrally formed from a suitable material, such as the shape memory materials discussed above. As illustrated, the body (204) of the staple (200) does not change shape between the unactivated state and the activated state. The staple (200) may be interlocked with a corresponding plate similar to the plate (102) above except with four holes for the legs (202), using the pinching engagement similar to the pinching engagement of the interlocked configuration in the fixation system (100) discussed above. This can provide at least four areas of interlocking engagement, with one for each of the four legs (202), pinching the plate between opposing pairs of legs. The beams (206) of the staple (200) may also bend in the activated state for the interlocked configuration, similarly to how the body (122) of the staple (104) bends to produce additional interlocking engagement areas in the interlocked configuration of the fixation system (100).

Figure 2:
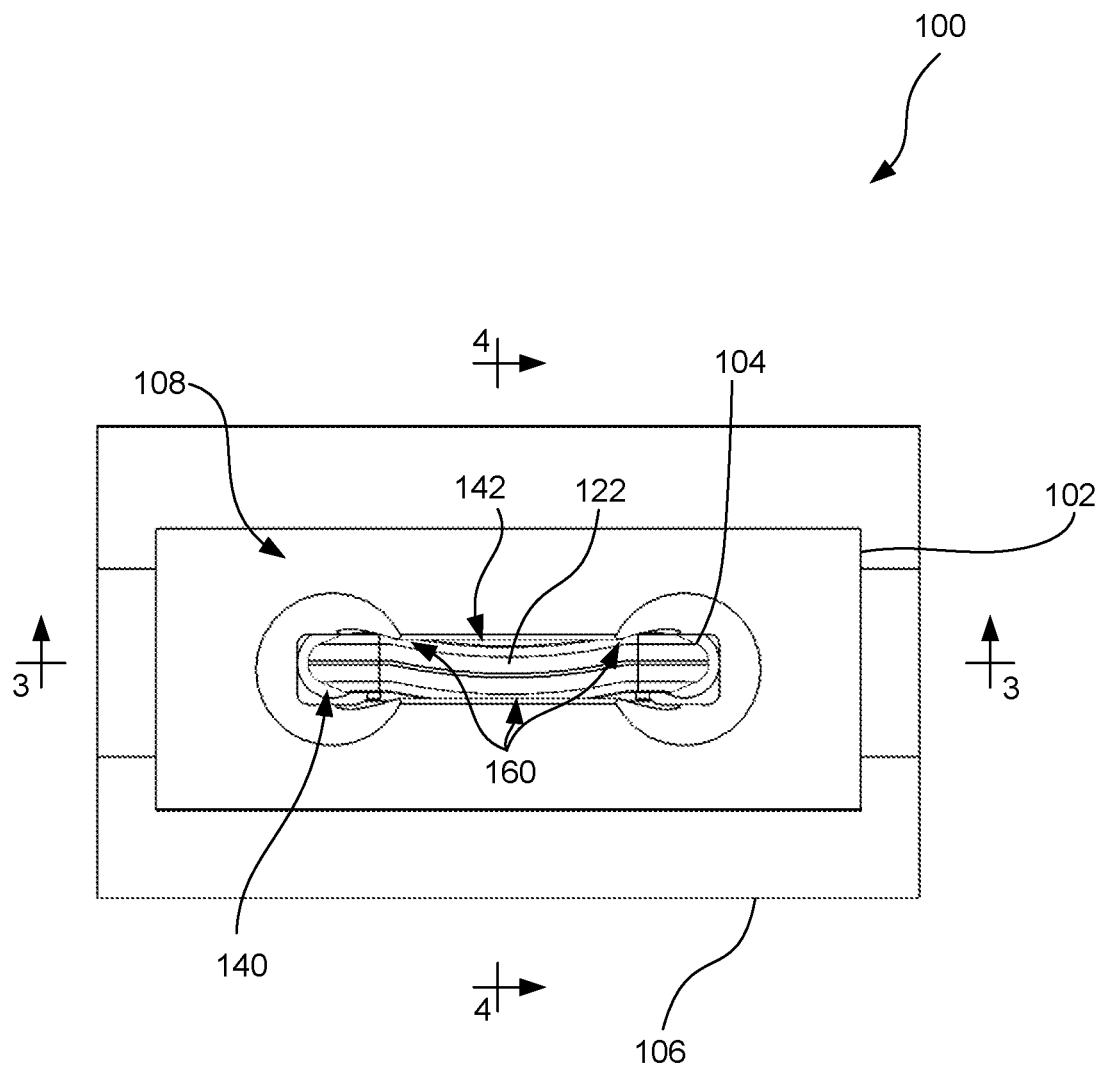
FIG. 2 is a top view of the fixation system and hard tissue of FIG. 1. Note that directional terms such as top, front, side, bottom, etc. are used herein with reference to the figures for convenience in describing the system. The system may be used in many different orientations, as is appropriate for using the fixation system for securing a plate to hard tissue in different circumstances.
Figure 20:
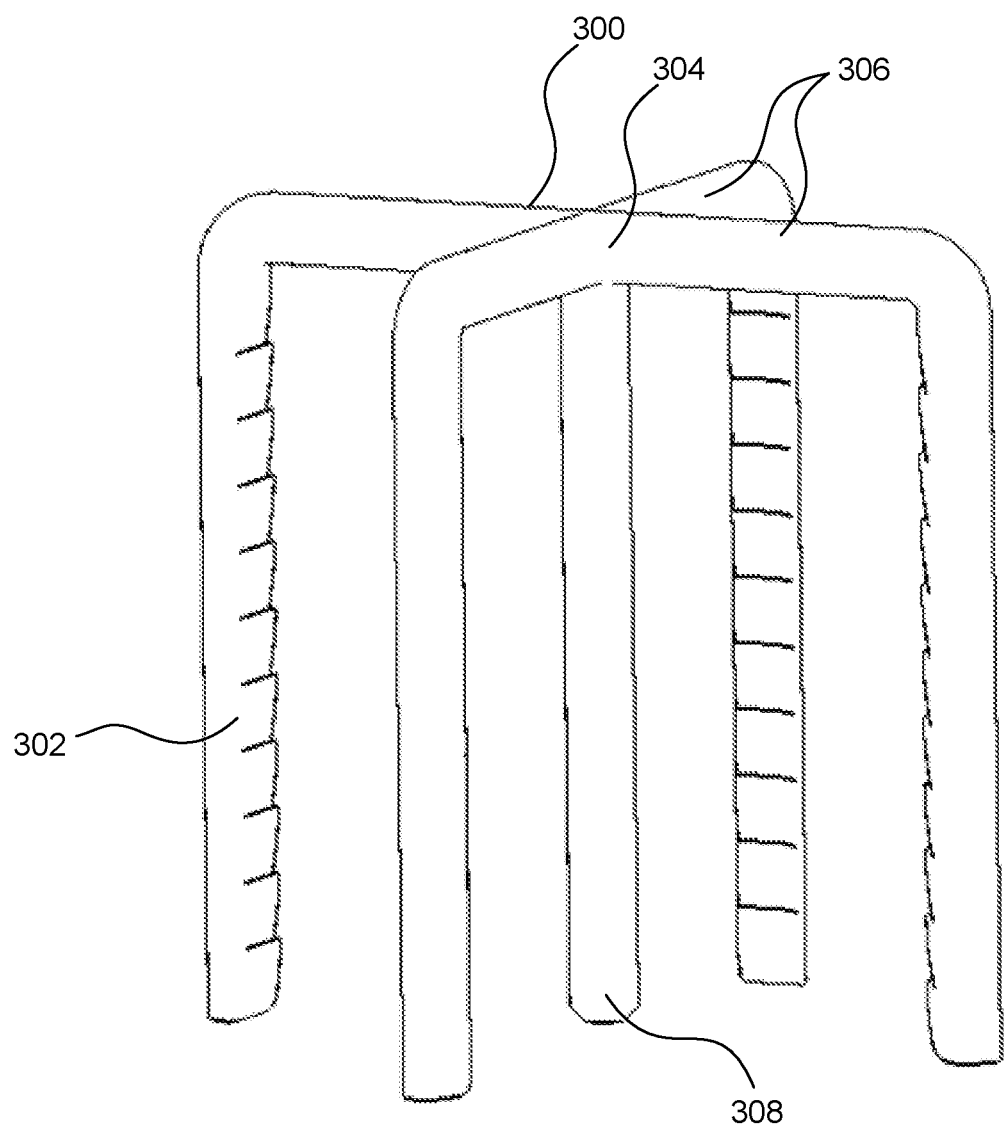
FIG. 20 is a perspective view of a five-prong staple in an unactivated state.
Figure 21:
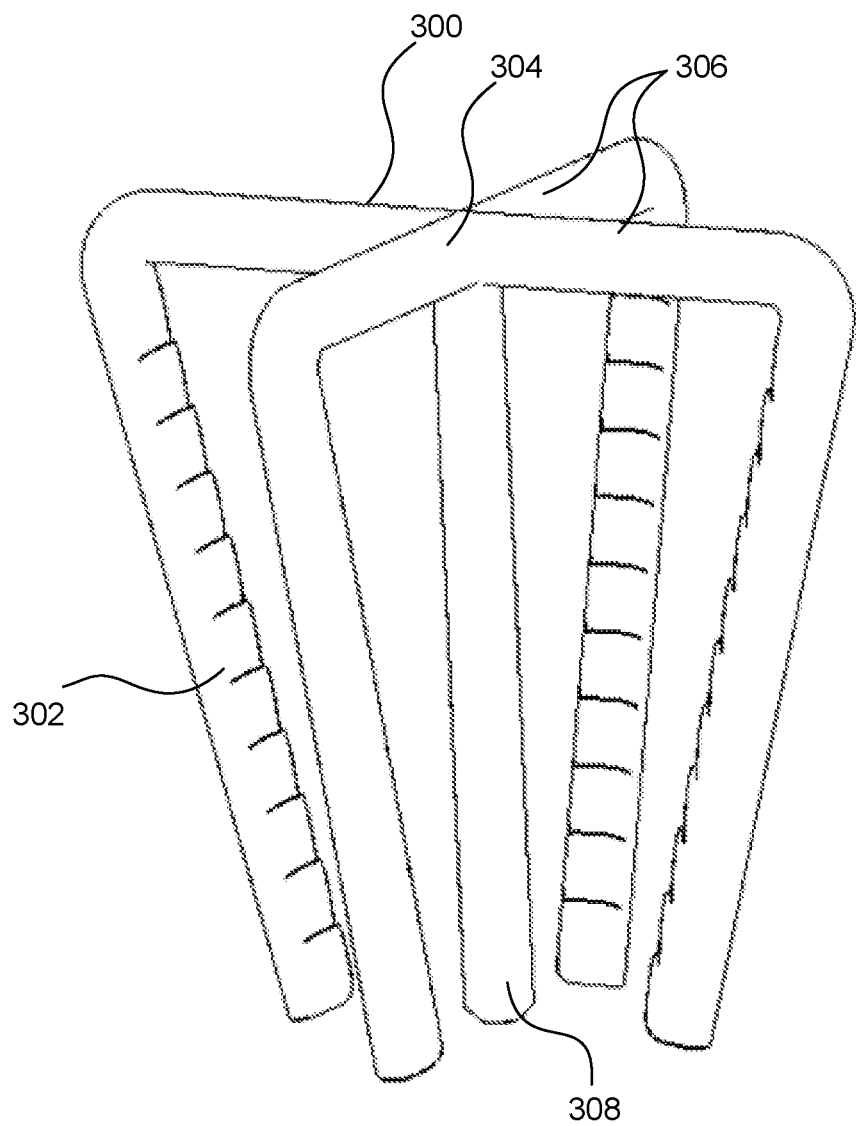
FIG. 21 is a perspective view of the five-prong staple of FIG. 20 in an activated state.

FIG. 20 illustrated a five-pronged staple (300) with four legs (302) and a body (304) that includes crossing beams (306), like the staple (200) of FIG. 2. The staple (300) also includes a pin (308) that extends in an insertion direction (parallel to the legs (302) in the unactivated state that can be used for an insertion configuration) from a central area of the body (304) where the crossing beams (306) are joined. The pin (308) can be considered a fifth leg, or fifth prong, of the staple (300). In the unactivated state illustrated in FIG. 20, the legs (302) and the pin (308) can be inserted through holes in a corresponding plate and into hard tissue. The staple (300) can transition to an activated state illustrated in FIG. 21, which can be used for an interlocked configuration, wherein the legs angle inwardly in the same manner as the legs (202) of the staple (200). As with the staple (200), the body (304) of the staple (300) could also bend to provide additional interlocking engagement areas, like the staple (104) discussed above. Also, each of the staples discussed herein, may be advantageously secured in hard tissue without a corresponding plate.

Figure 22:
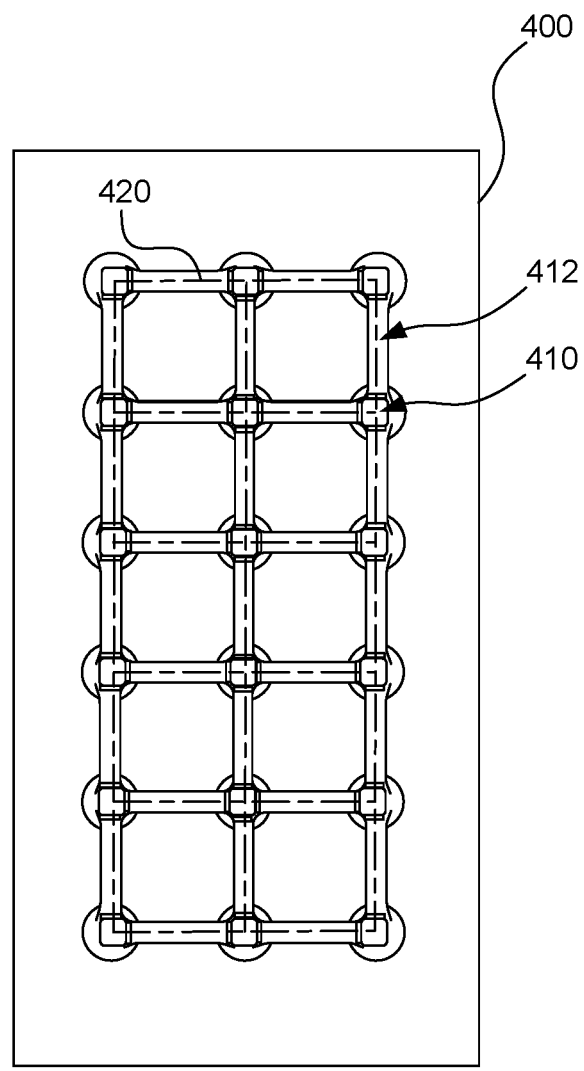
FIG. 22 is a top view of a plate that can be used in a fixation system with staples and/or screws.

V. Examples with Plates Having Additional Holes for Receiving Staples and/or Screws Other configurations of staples and plates may also be used with the novel features discussed herein. For example, FIG. 22 illustrates a plate (400) that can define 18 holes (410) like the holes (140) of the plate (102) discussed above, arranged in a three-by-six rectangular pattern. Grooves (412) can extend parallel and perpendicular to each other between the holes (410). The grooves (412) can be like the grooves (142) discussed above. Staples can be inserted in and interlock with the plate (400) in insertion configurations in ways like those discussed above and may be interlocked with the plate (102) in ways like those discussed above. For example, staples may be inserted in pairs of holes with lines (420) between centers of the holes being at non-parallel angles, such as being perpendicular, or with lines between them being parallel to each other. Accordingly, multiple two-pronged staples may be parallel to each other and/or perpendicular to each other, and the plate (400) may also receive staples having more than two prongs, as well as screws. The plate (400) may also receive two-pronged staples that span more than two holes.

Figure 23:
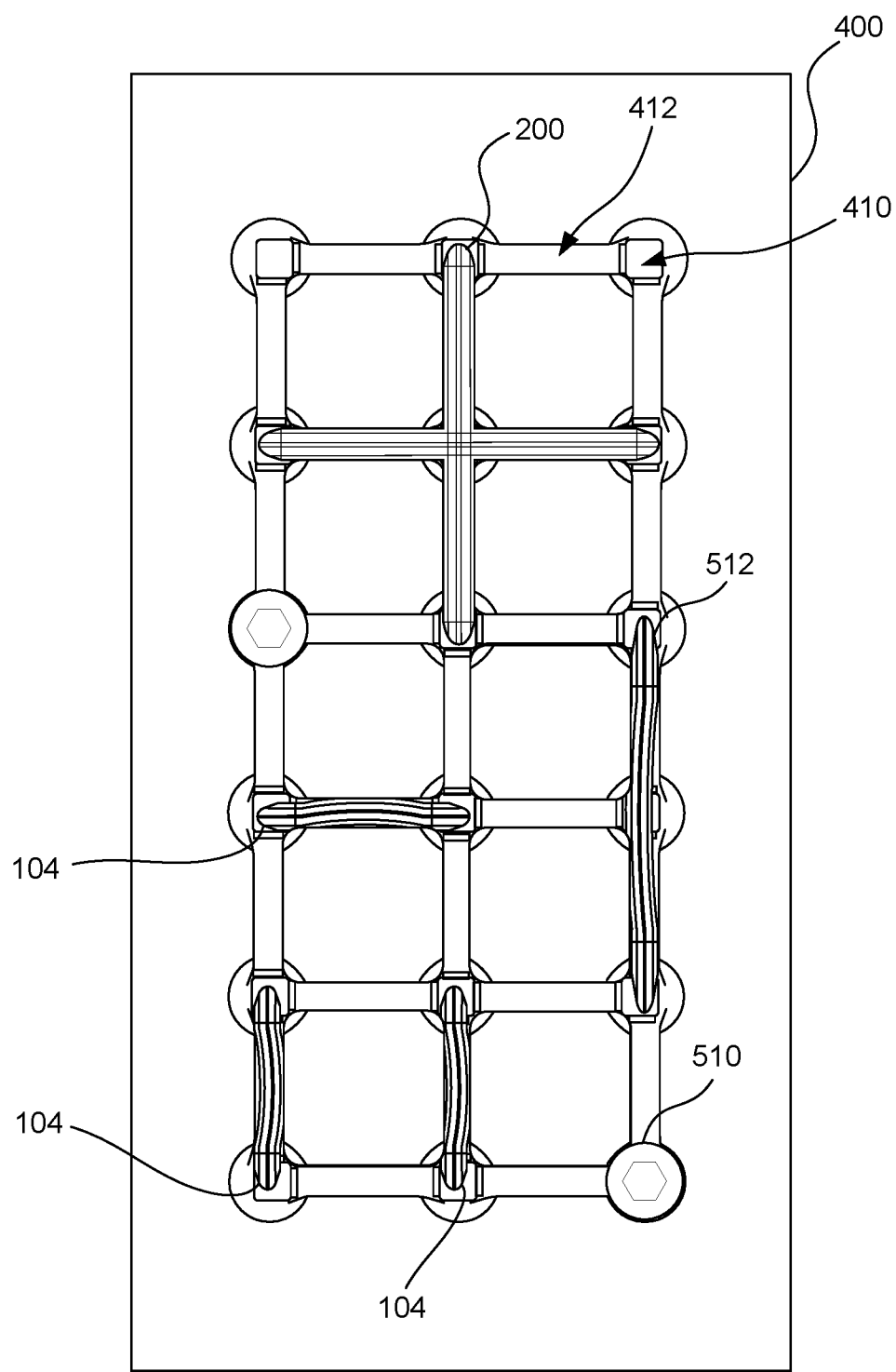
FIG. 23 is a top view of a fixation system using the plate of FIG. 22, in an interlocked configuration with two two-pronged staples, two screws, and one four-pronged staple.

Referring now to FIG. 23, a top view of a fixation system (500) is illustrated in an interlocked configuration. The fixation system (500) in this example includes the plate (400). The fixation system (500) also includes the four-pronged staple (200) discussed above with reference to FIGS. 18-19 interlocked with the plate (400), with opposite pairs of legs spanning three holes in the plate (400). The five-pronged staple (300) could be inserted in and interlocked with the plate (400) in a similar manner. Additionally, the fixation system (500) includes three two-pronged staples (104) like the staple (104) discussed above in the fixation system (100). The two-pronged staples (104) are interlocked with the plate (400) in the same manner that the staple (104) interlocked with the plate (102) in the fixation system (100) discussed above. In the example of FIG. 23, two of the two-pronged staples (104) are parallel to each other and a third two-pronged staple (104) is at a non-parallel angle to the other two two-pronged staples (104). Specifically, in this embodiment, the third two-pronged staple (104) is perpendicular to the other two two-pronged staples (104). Also, a two-pronged staple (512) can be the same as the staple (104) discussed above, but the two-pronged staple (512) can be configured so that it can span three or more holes in the plate (400). Thus, the legs of the staple (512) can extend into a pair of holes, and the plate can include one or more intermediate holes between that pair of holes, without legs of the staple (512) extending into those intermediate holes (or with legs of the staple extending into those intermediate holes if the staple includes more than two legs that are in line with each other). However, the intermediate holes can be configured to receive staple legs and/or screws (510), so that staple legs and/or screws can be inserted in such holes in other fastener arrangements.

The fixation system (500) also includes two screws (510), with each screw extending through one of the holes (410) and into the underlying hard tissue to which the plate (400) is fixed by the screws (510), the two-pronged staples (104) and the four-pronged staple (200). Other different configurations and combinations of plates, staples, and screws may be used in different circumstances, such as where different configurations of one or more bones and/or other soft tissue are being secured to a plate. The different types of fasteners (104, 200, 512, etc.) and the plate (400) that is configured to receive and interlock with these different fasteners in different arrangements can allow a clinician to uniquely configure a fixation system (500) in different ways to fit the needs of different procedures.

VI. Discussion of Hard Tissue Fixation Aspects and Features

Multiple aspects of the features discussed herein will now be described. The features discussed can be used in any combination with each other that is not foreclosed by the discussion herein.

According to one aspect, a hard tissue fixation system includes a plate defining a pair of holes formed therein, a staple including a body joining a pair of legs of the staple, and a staple-plate interlocking device. The staple-plate interlocking device can include a recess formed in one of the staple body or the plate, with recess surface portions formed thereon, and with the recess widening as it extends deeper into the recess. The interlocking device can also include a locking part of the other of the staple body or the plate, with the locking part having part surface portions formed thereon. The staple-plate interlocking device can be reconfigurable between an insertion configuration and an interlocked configuration. In the insertion configuration, the locking part can be configured to slide into the recess in a translation sliding motion that is parallel to a sliding motion of the legs of the staple, as the legs of the staple slide through the holes in the plate. In the interlocked configuration, the locking part can be at least partially in the recess, and the recess surface portions can engage the part surface portions and inhibit movement of the staple and plate out of the interlocked configuration, with the legs of the staple extending through the holes in the plate and being configured to extend into hard tissue adjacent to the plate.

The recess can be a groove in the plate, and the locking part can be the staple body. One of the locking part and the recess can have a different curvature in the insertion configuration than in the interlocked configuration. For example, the one of the locking part and the recess that has a different curvature in the different configurations can be formed of a shape memory alloy, and an original shape of the shape memory alloy can be a shape in the interlocked configuration.

As an example, where the recess is a groove in the plate and the locking part is the staple body, at least a portion of the staple body can have a different curvature in the insertion configuration than in the interlocked configuration. In this situation, a curvature of the at least a portion of the staple body can align with an opening of the groove in the insertion configuration, and the curvature of the at least a portion of the staple body can misalign with the opening of the groove in the interlocked configuration.

In the insertion configuration, the legs of the staple can be substantially parallel to each other, such as within five degrees of being parallel. In the interlocked configuration, the legs of the staple can angle inwardly toward each other as the legs extend in an insertion direction from the staple body and into the hard tissue. In the interlocked configuration, the plate can be pinched between the legs of the staple, at or adjacent to a base portion of each leg.

According to another aspect, a hard tissue fixation system can include a plate defining a first pair of holes formed therein and a second pair of holes formed therein. A line between centers of the first pair of holes can be at a non-parallel angle to a line between centers of the second pair of holes. The first staple can include a body joining a pair of legs that extend through the first pair of holes and are configured to extend into hard tissue. The second staple can include a body joining a pair of legs that extend through the second pair of holes and are configured to extend into hard tissue. Each hole in the first pair of holes can be configured to receive a screw. Also, the plate can further define an additional hole, and the fixation system can further include a screw that is configured to extend through the additional hole and into hard tissue. The first staple can include more than two legs, with each leg of the staple being configured to extend through a hole in the plate and into hard tissue.

The plate can define a first groove extending between the first pair of holes and a second groove extending between the second pair of holes. The body of the first staple can be configured to have a curvature that presses the body of the first staple against one or more surface portions defining the first groove to lock the body of the first staple to the plate in an interlocked configuration of the first staple. The body of the second staple can be configured to have a curvature that presses the body of the second staple against one or more surface portions defining the second groove to lock the body of the second staple to the plate in an interlocked configuration of the second staple. Also, the interlocked configuration of each staple can include the pair of legs of the staple, angling inwardly toward each other as the pair of legs of the staple extend in an insertion direction away from the body of the staple, pinching the plate between the pair of legs of the staple.

According to yet another aspect, a plate can be positioned adjacent to hard tissue, with the plate defining a pair of holes formed therein. A staple can be inserted, where the staple can have a pair of legs and a body joining the pair of legs. The inserting of the staple can include the pair of legs of the staple in an insertion direction through holes in the plate and into the hard tissue (which may have been drilled with pilot holes prior to insertion of the staple). A staple-plate interlocking device can be in an insertion configuration during the inserting. A locking part of one of the staple body and the plate and a recess of the other of the staple body and the plate can slide together in a translation motion in a direction parallel to the insertion direction. The staple-plate interlocking device can be transitioned from the insertion configuration to an interlocked configuration. The interlocked configuration can include the legs of the staple extending through the holes in the plate and into the hard tissue adjacent to the plate. The interlocked configuration can also include the locking part of one of the staple body and the plate being at least partially within the recess in the other of the staple body and the plate. Additionally, the interlocked configuration can include surface portions of the recess engaging with surface portions of the locking part, with the engaging of the surface portions inhibiting movement of the staple and plate out of the interlocked configuration.

The recess can be a groove in the plate. Also, one of the locking part and the recess can have a different curvature in the insertion configuration than in the interlocked configuration. The one of the locking part and the recess that has a different curvature can be formed of a shape memory alloy. An original shape of the shape memory alloy can be a shape in the interlocked configuration and transitioning the interlocking device to the interlocked configuration can include transitioning the shape memory alloy to the original shape. The recess can be a groove in the plate, and at least a portion of the staple body can have a different curvature in the insertion configuration than in the interlocked configuration. Also, in the interlocked configuration, the plate can be pinched between the legs of the staple, adjacent to a base portion of each leg. The interlocked configuration can include at least five separate areas of engagement between the staple and the plate, with each of the five separate areas of engagement contributing to inhibiting movement of the staple and the plate out of the interlocked configuration.

While the invention has been particularly shown and described with reference to preferred embodiments thereof, it will be understood by those skilled in the art that various changes in form and details may be made therein without departing from the spirit and scope of the invention.

I claim:

1. A hard tissue fixation system comprising:
a plate comprising a first hole, a second hole, a third hole, a fourth hole, a first groove, a second groove, a third groove, and a fourth groove, wherein the first groove extends from the first hole to the second hole, and wherein the first groove comprises a base, a first wall, a second wall, an opening, and a cross-section having a first shape; and
a staple comprising a first leg, a second leg, a third leg, a fourth leg, a first body extending from the first leg to the second leg, and a second body extending from the third leg to the fourth leg, wherein the first body comprises a cross-section that corresponds to the cross-section of the first groove;
wherein the first staple body intersects with the second staple body; and wherein the staple further comprises a fifth leg that extends from the intersection of the first and second staple bodies;
wherein the staple is inserted into the plate in an insertion configuration in which the staple first body has a first shape such that the first staple leg is inserted into the first plate hole, the second staple leg is inserted into the second plate hole, and the first body is inserted into the first groove;
wherein the staple interlocks with the plate in an interlocking configuration after the staple has been inserted into the plate; and
wherein in the interlocking configuration the first body has a second shape in which the cross-section of the first body engages with the corresponding cross-section of the first groove at an engagement area.

2. The hard tissue fixation system of claim 1, wherein the engagement area comprises a first body engagement area, a second body engagement area, and a third body engagement area.

3. The hard tissue fixation system of claim 1, wherein in the insertion configuration the first and second staple legs are parallel and extend at a first angle that is perpendicular to an axis of the first body.

4. The hard tissue fixation system of claim 1, wherein the first staple body intersects with the second staple body at a right angle.

5. A hard tissue fixation system comprising:
a plate comprising a first hole, a second hole, a third hole, a fourth hole, a first groove, a second groove, a third groove, and a fourth groove, wherein the first groove extends from the first hole to the second hole, and wherein the first groove comprises a base, a first wall, a second wall, an opening, and a cross-section; and a staple comprising a first body extending from a first leg to a second leg and a second body extending from a third leg to a fourth leg, wherein the second body intersects the first body, and wherein the first body comprises a cross-section that corresponds to the cross-section of the first groove;

wherein the staple is inserted into the plate in an insertion configuration in which the first body has an insertion shape such that the first staple leg is inserted into the first plate hole, the second staple leg is inserted into the second plate hole, and the first body is inserted into the first groove;

wherein the staple interlocks with the plate in an interlocking configuration after the staple has been inserted into the plate;

wherein in the interlocking configuration the first body has an interlocking shape in which the cross-section of the first body engages with the corresponding cross-section of the first groove at an engagement area; and wherein in the interlocking configuration the first and second staple legs are angled such that the first and second legs are not parallel to each other; and wherein the third and fourth staple legs are angled such that the third and fourth legs are not parallel to each other; and wherein the staple further comprises a fifth leg that is parallel to a longitudinal central axis of the staple.

6. A hard tissue fixation system comprising:

a plate comprising a first hole, a second hole, a third hole, a first groove connecting the first hole with the second hole, and a second groove connecting the second hole with the third hole, wherein each of the first groove and the second groove comprises a floor having a first width, a first wall, a second wall, and an opening having a second width that is less than the first width; and a staple comprising a first leg, a second leg, and a body extending from the first leg to the second leg, wherein the staple body comprises a cross-section corresponding to a cross-section of the first groove, the staple body cross-section having a base, a first face, and a second face;

wherein a width of the staple body base is less than the second width of the first groove opening;

wherein the staple is inserted into the plate in an insertion configuration in which the staple body has a first configuration such that the first staple leg is inserted into the first plate hole, the second staple leg is inserted into the second plate hole, and the staple body is inserted into the first plate groove;

wherein the staple interlocks with the plate in an interlocking configuration after the staple has been inserted into the plate;

wherein in the interlocking configuration the staple body has a second configuration, in which the first face of the staple body engages with the first wall of the first groove at a first engagement area; and wherein the change in configuration from the first configuration to the second configuration impairs removal of the staple from the first plate groove and from the first hole and the second hole of the plate.

7. The hard tissue fixation system of claim 6, wherein in the insertion configuration, the body of the staple is aligned with the first groove, and wherein the body of the staple is narrower than the opening in the first groove such that the staple may be inserted into the first groove.

8. The hard tissue fixation system of claim 7, wherein the staple first body extends straight from the first leg to the second leg without curving when the staple body is in the insertion configuration; and wherein the staple body extends from the first leg to the second leg with curving when the staple body is in the interlocking configuration.

9. The hard tissue fixation system of claim 7, wherein in the interlocking configuration, the body of the staple is non-aligned with the first groove such that an incongruity between an alignment of the first body and an alignment of the first groove impairs removal of the staple from the plate.

10. The hard tissue fixation system of claim 6, wherein the third hole is configured to accommodate a screw or a leg of a staple.

11. The hard tissue fixation system of claim 10, wherein in the interlocking configuration the second face of the staple body engages with the second wall of the first groove at a second engagement area; and wherein in the interlocking configuration the first face of the staple body further engages with the first wall of the first groove at a third engagement area.

12. The hard tissue fixation system of claim 6, wherein the plate comprises a fourth hole positioned between the first hole and the second hole; and wherein the staple body extends in the first groove from the first leg positioned in the first hole to the second leg positioned in the second hole passing over the fourth hole.

13. The hard tissue fixation system of claim 6, wherein the plate further comprises a fourth hole, a fifth hole, a third groove, a fourth groove, and a fifth groove.

14. The hard tissue fixation system of claim 6, wherein in the insertion configuration the first and second staple legs are parallel and extend at a first angle that is perpendicular to an axis of the staple body.

15. The hard tissue fixation system of claim 6, wherein the second groove is collinear with the first groove.

* * * * *